(12) United States Patent
Mulla et al.

(10) Patent No.: US 9,447,033 B2
(45) Date of Patent: Sep. 20, 2016

(54) POTASSIUM CHANNEL BLOCKERS

(71) Applicant: Japan Tobacco Inc., Tokyo (JP)

(72) Inventors: Mushtaq Mulla, Cambridge (GB);
Derek Edward John, Cambridge (GB);
Richard John Hamlyn, Ely (GB);
Sasha Louise Garrett, Cambridge (GB); Basil Hartzoulakis, Cambridge (GB); David Madge, Ely (GB); John Ford, St. Ives (GB)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 14/724,195

(22) Filed: May 28, 2015

(65) Prior Publication Data

US 2015/0259282 A1 Sep. 17, 2015

Related U.S. Application Data

(62) Division of application No. 14/174,241, filed on Feb. 6, 2014, now Pat. No. 9,073,834, which is a division of application No. 12/550,860, filed on Aug. 31, 2009, now Pat. No. 8,673,901.

(60) Provisional application No. 61/093,233, filed on Aug. 29, 2008.

(30) Foreign Application Priority Data

Aug. 29, 2008 (GB) .................................. 0815782.8

(51) Int. Cl.

| C07D 207/12 | (2006.01) |
|---|---|
| C07D 209/08 | (2006.01) |
| C07D 211/16 | (2006.01) |
| C07D 211/44 | (2006.01) |
| C07D 213/44 | (2006.01) |
| C07D 213/71 | (2006.01) |
| C07D 403/12 | (2006.01) |
| C07D 401/12 | (2006.01) |
| C07C 317/40 | (2006.01) |
| C07C 311/21 | (2006.01) |
| C07C 311/46 | (2006.01) |
| C07D 213/40 | (2006.01) |
| C07D 231/12 | (2006.01) |
| C07D 231/18 | (2006.01) |
| C07D 231/56 | (2006.01) |
| C07D 233/61 | (2006.01) |
| C07D 233/84 | (2006.01) |
| C07D 265/30 | (2006.01) |
| C07D 265/36 | (2006.01) |
| C07D 271/08 | (2006.01) |
| C07D 277/36 | (2006.01) |
| C07D 277/46 | (2006.01) |

(Continued)

(52) U.S. Cl.
CPC ............ *C07C 311/21* (2013.01); *C07C 311/46* (2013.01); *C07C 317/32* (2013.01); *C07C 317/40* (2013.01); *C07D 207/12* (2013.01); *C07D 209/08* (2013.01); *C07D 211/16* (2013.01); *C07D 211/34* (2013.01); *C07D 211/44* (2013.01); *C07D 213/36* (2013.01); *C07D 213/40* (2013.01); *C07D 213/71* (2013.01); *C07D 231/12* (2013.01); *C07D 231/18* (2013.01); *C07D 231/56* (2013.01); *C07D 233/61* (2013.01); *C07D 233/64* (2013.01); *C07D 233/84* (2013.01); *C07D 265/30* (2013.01); *C07D 265/36* (2013.01); *C07D 271/08* (2013.01); *C07D 277/28* (2013.01); *C07D 277/36* (2013.01); *C07D 277/46* (2013.01); *C07D 285/12* (2013.01); *C07D 285/135* (2013.01); *C07D 307/79* (2013.01); *C07D 311/70* (2013.01); *C07D 317/62* (2013.01); *C07D 319/18* (2013.01); *C07D 401/12* (2013.01); *C07D 403/12* (2013.01); *C07D 413/12* (2013.01); *C07C 2101/02* (2013.01); *C07C 2101/04* (2013.01); *C07C 2101/08* (2013.01)

(58) Field of Classification Search
CPC ............ C07D 2017/12; C07D 209/08; C07D 211/16; C07D 211/44; C07D 213/40; C07D 213/71; C07D 403/12; C07D 413/12; C07D 401/12; C07C 317/40; C07C 311/21; C07C 311/46
USPC ........ 544/105, 160, 370; 546/221, 290, 226; 548/366.1, 316.4; 514/237.5, 254.05, 514/230.5, 407, 398, 345
See application file for complete search history.

(56) References Cited

U.S. PATENT DOCUMENTS 7,084,160 B2 * 8/2006 Borzilleri et al. ............ 514/342

*Primary Examiner* — Kahsay Habte
(74) *Attorney, Agent, or Firm* — Leydig, Voit & Mayer, Ltd.

(57) ABSTRACT

The present invention provides a compound of formula (I)

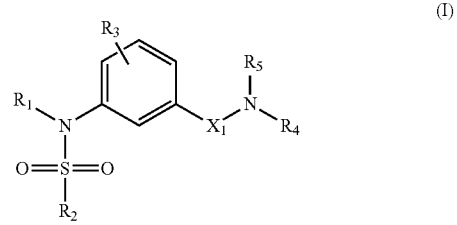

or its salts or pharmaceutically acceptable derivatives thereof wherein $X_1$, $R_1$, $R_2$, $R_3$, $R_4$, and $R_5$ are defined as set forth in the specification. The compounds are useful as potassium ion channel inhibitors.

20 Claims, No Drawings

(51) Int. Cl.
*C07D 285/135* (2006.01)
*C07D 307/79* (2006.01)
*C07D 311/70* (2006.01)
*C07D 317/62* (2006.01)
*C07D 319/18* (2006.01)
*C07D 413/12* (2006.01)
*C07C 317/32* (2006.01)
*C07D 211/34* (2006.01)
*C07D 233/64* (2006.01)
*C07D 285/12* (2006.01)
*C07D 213/36* (2006.01)
*C07D 277/28* (2006.01)

POTASSIUM CHANNEL BLOCKERS

FIELD OF THE INVENTION

The present invention relates to compounds of formula (I) which are potassium channel inhibitors. Compounds in this class may be useful as Kv1.3 inhibitors for immunomodulation and the treatment of autoimmune, chronic inflammatory, metabolic diseases and the like. Additionally, compounds in this class may also be useful as Kv1.5 inhibitors for the treatment or prevention of arrhythmias. Pharmaceutical compositions comprising the compounds and their use in the treatment of autoimmune and inflammatory diseases and in the treatment of arrhythmia are also provided.

BACKGROUND

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature, see Gutman et al., 2003).

Compounds which modulate potassium channels have multiple therapeutic applications in several disease areas including autoimmune, inflammatory, cardiovascular, neuronal, auditory, renal and metabolic mediated diseases (Shieh et al., 2000; Ford et al., 2002, Xie al, 2004, Cahalan at al, 1997). The potassium channel Kv1.3 is found in a number of tissues including neurons, blood cells, osteoclasts; macrophages, epithelia, and T- and B-lymphocytes. Furthermore, Kv1.3 inhibition has been shown to modulate T-cell function which has implications in many autoimmune diseases including psoriasis, rheumatoid arthritis, multiple sclerosis, obesity, diabetes and inflammatory bowel disease (Becton et al., 2006).

Kv1.3 Channel Blockers for Autoimmune Disorders

The role of autoreactive, late-stage, memory T-cells in the pathogenesis of a variety of autoimmune diseases including psoriasis, rheumatoid arthritis, multiple sclerosis, IBD and others is well established. Activation of $T_{EM}$ cells is followed by substantial up-regulation of Kv1.3 channel expression and, as a result, Kv1.3 becomes the predominant route of potassium efflux from the cell. Thus, selective blockade of Kv1.3 causes membrane depolarisation and inhibition of $Ca^{2+}$ influx, leading to inhibition of cytokine production and cell proliferation and function. Kv1.3 thus represents a novel therapeutic target of great interest for autoimmune disease control.

T-Cells and Autoimmunity

T-cells are lymphocytes which play a central role in cell mediated immunity. One of the major forms of T-cell is the helper T-cell ($T_H$), also known as CD4+ cells which plays an essential role in the development of autoimmune diseases. Through the production of the cytokine interleukin 2 (IL-2), CD4+ T-cell can create the second main type of T-cell known as cytotoxic T-cells (CD8+). Naïve (inactive) CD4+ and CD8+ T-cells express both proteins (CCR7+CD45RA+) and use the chemokine receptor CCR7 as a key to gain entry into lymph nodes. Within lymph nodes, the naïve T-cells encounter antigen and through an activation process, change into "effector" T-cells that produce cytokines and proliferate. Once the ensuing immune response subsides, most naïve effectors die, but a few differentiate into long-lived central memory cells ($T_{CM}$). $T_{CM}$ cells, like naïve cells, use CCR7 to home to the lymph nodes to encounter their cognate antigen. Upon antigenic stimulation, $T_{CM}$ cells change into "$T_{CM}$ effector" cells that produce cytokines and proliferate. They too suffer the same fate as naïve effectors, the majority dying after the immune response wanes, leaving a few long-lived survivors for farther challenge. Repeated antigenic challenge, as might happen in autoimmune diseases or in chronic infections, causes $T_{CM}$ cells to differentiate into short-lived "effector memory T-cells" ($T_{CM}$) that lack expression of both CCR7 and CD45RA, and do not need to home to lymph nodes for antigen-induced activation. A subset of CD8+ $T_{EM}$ cells reacquire CD45RA and become CCR7-CD45RA+ $T_{EMRA}$ cells. Upon activation, both CD4+ and CD8+ $T_{PM}$ cells change into $T_{EM}$ effectors that migrate rapidly to sites of inflammation and produce large amounts of the proinflammatory cytokines, interferon-γ (IFN-γ) and tumor necrosis factor α (TNFα). In addition, CD8+ $T_{EM}$ effectors carry large amounts of perforin and are therefore immensely destructive (Wulff et al, 2003, Becton et al, 2005).

Functional Role of Kv1.3 in T-cells and Autoimmune Disorders

Human T-cells express two $K^+$ channels, Kv1.3 and IKCa1, that provide the counterbalance cation efflux necessary for the sustained elevation of cytosolic $Ca^{2+}$ levels required for gene transcription, proliferation and cytokine secretion (Panyi et al, 2004, Chandy et al, 2004). The Kv1.3 and IKCa1 (also known as KCa3.1) channels regulate membrane potential and facilitate $Ca^{2+}$ in T-lymphocytes. Kv1.3 opens in response to membrane depolarisation and maintains the resting membrane potential (initiation phase), whereas IKCa1 opens in response to an increase in cytosolic $Ca^{2+}$ hyperpalarises the membrane potential (Becton et al, 2001). Selective blockade of $K^+$ channels leads to membrane depolarisation, which in turn inhibits $Ca^{2+}$ influx and shuts down cytokine production and cell proliferation. Early in vitro studies, using channel blocker toxins, clearly demonstrate that Kv1.3 channels are essential for the synthesis (gene activation) and secretion of the cytokine IL-2 after T-cell activation (Price et al, 1989) and provide a rationale for the potential therapeutic use of inhibitors of this channel in immunological disorders. The role of autoreactive T-cells in the pathogenesis of autoimmune diseases has clearly been demonstrated in animal models. Disease-specific, autoreactive T-cells in several other autoimmune diseases are also reported to exhibit as memory phenotype. Autoreactive $T_{EM}$ cells arc also implicated in psoriasis, rheumatoid arthritis, multiple sclerosis, IBD, vitiligo, uveitis, pemphigus, inflammatory myopathics, Hashimito disease, and scleroderma (Becton et al, 2005). "Late" memory T- and B-cells have been implicated in the disease progression and tissue damage in a number of autoimmune diseases, in transplant rejection and chronic graft-versus-host disease. Modulators of the Kv1.3 channel may allow selective targeting of disease-inducing effector memory T-cells and memory B-cells without compromising the normal immune response and as a result are likely to have a preferred side-affect profile than agents that bring about more general immmosuppression.

The observation that the Kv1.3 blocker margatoxin (mgTX) effectively suppressed the delay-type hypersensitivity (DTH) response in vivo was provided by Koo et al, 1999. In addition MgTX was also shown to inhibit primary antibody response in non-sensitised animals (secondary antibody response was not affected by MgTX. These latter results are in agreement with the notion that Kv1.3 channels are predominant in resting T lymphocytes and regulate their function, while IKCa1 channels are more important in pre-activated T lymphocytes. Correotide (Koo et al, 1999) and PAP-1 (Schmitz et al, 2005) arc novel immunosuppressants which block Kv1.3 channels and are effective in the DTH model. Because the cellular components involved in DTH response are similar to those found in autoimmune diseases and allograft rejection, the results obtained are very promising for the development of Kv1.3 channel blockers as new immunosuppressants.

In the early 1980s a number of compounds were reported to block Kv1.3 channels at micromolar to millimolar concentrations as described by Triggle et al, in "Voltage Gated Ion Channels as Drug Targets" these include classical Kv channel inhibitors such as 4-aminopyridine and tetramethylammonium and other non specific compounds such as the calcium activated potassium channel blockers quinine and ceteidil, the phenothiazine antipscychotics chloropromazine and trifluoroperazine, the classical calcium channel inhibitors verapamil, diltiazem, nifedipine and nitrendipine, and the beta blocker propranolol.

Also in the 1980's natural products extracted from scorpions, snakes and other marine organisms were found to be potent inhibitors of Kv1.3 channels, these were primarily short peptides (<70 residues) that are stabilised by multiple sulphide bonds. The first of these potent inhibitors was isolated from the venom of the scorpion *Leiurus quinquestricans hebraeus* and was named charybdotoxin (ChTX) (Sands et al, 1989), there after screening of other scorpion venoms led to the identification of more potent Kv1.3 blocking toxins, these include margatoxin (MgTX) (Garcia et 1993), ugitoxin-2 (Garcia et al, 1994), hongotoxin (Koshchak et al.), paudinus imperator toxin 2 (Pi2) (Peter et al, 2001) and orthochirus scrobiculosus (OSK1) (Mouhat et al, 2005) among others. With the exception of OSK1 (300 fold selective over the nearest related channel) none of the scorpion toxins were selective for Kv1.3.

One of the most potent and selective Kv1.3 blockers to date, which was extracted from sea anemone is *stichodactyla helianthus* toxin (Shk) (Pennington et al, 1996) this has been reported for the treatment of autoimmune disease through the blockade of Kv1.3 (U.S. Pat. No. 6,077,680). Shk and its synthetic derivative Shk-Dap$^{22}$ with improved selectivity profile display pico molar activity (Pennington et al, 1998) however, these peptides proved to have unfavourable properties for further development.

Recently more novel and selective small molecule Kv1.3 channel blockers have been reported for the management of autoimmune disorders. These include the iminodihydroquinolines WIN173173 and CP339818 (Nguyen et al., 1996), the benzohydrol piperidine UK-78,282 (Hanson et al. 1999), corrcolide (Felix et al., 1999), cyclohexyl-substituted benzamide PAC (U.S. Pat. No. 6,194,458, WO0025774), sulfamidebenzamidoindane (U.S. Pat. No. 6,083,986), Khellinone (Baell et al., 2004), dichloropenylpyrazolopyrimidine (WO-00140231) and psoralens (Wulff et al., 1998, Vennekamp et al., 2004, Schmitz et al., 2005).

Furthermore, the related KV1.5 channel is expressed in atrial myocytes and is believed to offer therapeutic opportunities for the management of atrial fibrillation for several different reasons (see review of Brendel and Peukert, 2002); (i) There is evidence that Kv1.5 underlies the cardiac ultrarapid delayed rectifier ($Kv_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng at al., 1997). (ii) electrophysiological recordings have demonstrated that $Kv_{(ur)}$ is selectively expressed in atrial myocytes, and therefore avoids inducing potentially fatal ventricular arrhythmia through interfering with ventricular repolarisation (Amos at al. 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Drugs that maintain the sinus rhythm long-term without proarrhythmic or other side effects are highly desirable and not currently available. Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in viva canine models (Matsuda et al., 2001), and S9947 inhibited Kv1.5 stably expressed in both *Xenopus oocytes* and Chinese hamster ovary (CHO) cells and $Kv_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et al 2003), thiophene carboxylic acid amides (WO0248131), bisaryl derivatives (WO0244137, WO0246162), carbonamide derivatives (WO0100573, WO0125189) anthranillic acid amides (WO2002100825, WO02088073, WO02087568), dihydropyrimidines (WO0140231), cycloalkylamine derivatives (WO2005018635), isoquionolines (WO2005030791), quinolines (WO2005030792), imidazopyrazines (WO205034837), benzopyranols (WO2005037780), isoquinolinones (WO2005046578), cycloakyl derivatives (WO03063797), indane derivatives (WO0146155 WO9804521), tetralin benzocycloheptane derivatives (WO9937607), thiazolidone and metathiazanone derivatives (WO99962891), benzamide derivatives (WO0025774), isoquinoline derivatives (WO0224655), pyridazinone derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

Sulfonamides have been reported to be useful as inhibitors of 11-beta-hydroxysteroid dehydrogenase type1, CCR5, H3 receptor and mitotic kinesins amongst others.

Substituted aryl tertiary sulfonamides, wherein position 4 is substituted with an amide have been claimed as inhibitors of 11-betehydroxysteroid dehydrogenase type1, for the treatment and prevention of hyperglycemia in diseases such as type-2 diabetes (WO2004065351), Substituted aryl tertiary sulfonamides, wherein position 3 is optionally substituted with substituted alky, alkoxyamino, sulfonyl, acyl, alkoxy carbonyl or aminocarbonyl have been claimed as inhibitors of mitotic kinesins as effective anti cancer agents (WO2007056078).

Substituted 1-3 phenyl sulfonamides bearing a benzyl group and an amido group have been claimed as useful for the treatment and/or prophylaxis of viral diseases, in particular for the treatment of Hepatitis C (WO 2007/110171)

Elsewhere, arylsulophonylaminobenzene derivatives bearing an alkylamino group meta to the sulfonamide were found to be inhibitors of Factor Xa and useful in the treatment of arterial and venous thrombotic occlusive disorders, inflammation, cancer and neurodegenerative diseases (WO 96/40100).

Substituted 1,3 phenylsulfonamides containing an amido group meta to the sulfonamide have been claimed as inhibitors of BACE as an effective means for treating and preventing Alzheimer's and related diseases caused by the production of beta-amyloid (WO 2005/030709).

Substituted 1,3 phenylsulfonamides containing an ether group meta to the sulfonamide have also been claimed as liver X receptor (LXR) modulators useful for the treatment or prevention of diseases associated with the activity of LXR's (WO2003082205)

It has now surprisingly been found that compounds of general formula (I) set out below act as inhibitors of potassium channels. These compounds are particularly useful for inhibiting the potassium channel Kv1.3 and treating diseases associated with the inhibition of the potassium channel Kv1.3. This invention is not limited to treating diseases mediated by Kv1.3, the compounds also being useful to treat diseases which require Kv1.5 potassium channel inhibition for example atrial fibrillation (Marban, 2002, Brendel and Peukert, 2002).

Thus, in a first aspect, the present invention provides a compound of formula (I)

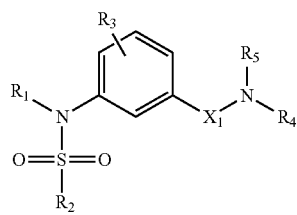

(I)

or its salts or pharmaceutically acceptable derivatives thereof wherein;

$X_1$ is selected from a group consisting of $CH_2$, $C(=O)$, $C(=NH)$, $NC(=O)$, $R_1$ is selected from the group consisting of optionally substituted arylalkyl, and optionally substituted heteroarylalkyl $R_2$ is selected from the group consisting of optionally substituted alkyl, optionally substituted aryl or heteroaryl or $NR_{24}R_{25}$ $R_3$ is selected from the group consisting of hydrogen, halogen, hydroxyl, alkoxy, aryloxy, optionally substituted alkyl, optionally substituted amino, optionally substituted amino sulfonyl or nitrile;

$R_4$ is selected from the group consisting of optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl $R_5$ may be hydrogen, an optionally substituted alkyl, preferably $CH_3$ or, $NR_4R_5$ may form an optionally substituted saturated or partially saturated 4-7 membered ring with the general formula (II).

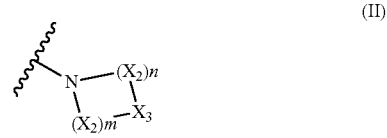

(II)

Wherein;

$X_2$ is $C(=O)$, $CH_2$, $CH(R_6)$ or $C(R_6)(R_6)$, $X_3$ is $CH_2$, $CH(R_7)$, $C(R_7)(R_7)$, NH, $N(R_8)$, O or S

Each $R_6$ independently represents optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;

Each $R_7$ independently represents optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl $R_8$ is optionally substituted acyl, optionally substituted alkyl, optionally substituted cycloalkyl, optionally substituted arylalkyl, optionally substituted aryl or optionally substituted heteroaryl;

$R_{24}$ and $R_{25}$ are the same or different and each represents hydrogen, optionally substituted alkyl, optionally substituted cycloalkyl, optionally substituted arylalkyl, optionally substituted aryl or optionally Substituted heteroaryl, n=1 or 2 m=1, 2 or 3

With the proviso that when $X_1$ is $C=O$ and $R_5$ is H then $R_4$ is not:

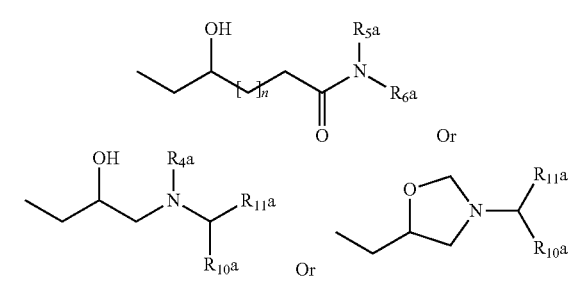

Where $R_4a$, $R_5a$ and $R_6a$ are each independently H, $C_{1-6}$alkyl, aryl, heteroaryl, cycloalkyl, or aryl-$C_{1-6}$alkyl;

$R_{10}a$ is H or $C_{1-6}$alkyl; and $R_{11}a$ is $C_{1-6}$alkyl or aryl-$C_{1-6}$alkyl and when $X_1$ is $C=O$ or $CH_2$ and $R_5$ is H then $R_4$ is not;

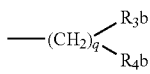

Where q is 0 to 5,
R$_3$b is H, OH or alkoxy and
R$_4$b is NH$_2$, phenyl or a C$_{3-10}$ heterocycle,
In one embodiment the invention provides compounds of the following formula:

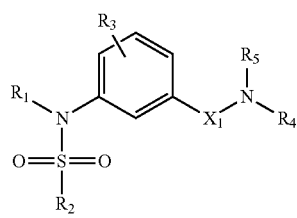

(I)

or its salts or pharmaceutically acceptable derivatives thereof wherein;

X$_1$ is Selected from a group consisting of CH$_2$, C(=O), C(=NH), NC(=O),

R$_1$ is selected from the group consisting of optionally substituted arylalkyl, and optionally substituted heteroarylalkyl R$_2$ is selected from the group consisting of optionally substituted alkyl, optionally substituted aryl or heteroaryl for NR$_{24}$R$_{25}$ R$_3$ is selected from the group consisting of hydrogen, halogen, hydroxyl, alkoxy, aryloxy, optionally substituted alkyl, optionally substituted amino, optionally substituted amino sulfonyl or nitrile;

R$_4$ is selected from the group consisting of optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl R$_5$ is may be hydrogen, an optionally substituted alkyl, preferably CH$_3$ or NR$_4$R$_5$ may form an optionally substituted saturated or partially saturated 4-7 membered ring with the general formula (II).

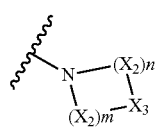

(II)

Wherein;
X$_2$ is C(=O), or C(R$_6$)$_2$,
X$_3$ is C(R$_7$), NH, N(R$_8$), O or S
R$_6$ for each occurrence independently represents hydrogen, optionally substituted amino, optionally Substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;
R$_7$ for each occurrence independently represents hydrogen, optionally substituted amino, optionally substituted amino carbonyl, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl;

R$_8$ optionally substituted acyl, optionally substituted alkyl, optionally substituted cycloalkyl, optionally substituted arylalkyl, optionally substituted aryl or optionally substituted heteroaryl;

R$_{24}$ and R$_{25}$ are the same or different and each represents hydrogen, optionally substituted alkyl, optionally substituted cycloalkyl, optionally substituted arylalkyl, optionally substituted aryl or optionally substituted heteroaryl, n=1 or 2
m=1, 2 or 3

With the proviso that when X$_1$ is C=O and R$_5$ is H then R$_4$ is not:

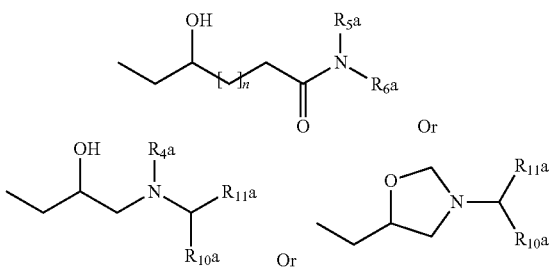

Where R$_4$a, R$_5$a and R$_6$a are each independently H, C$_{1-6}$alkyl, aryl, heteroaryl, cycloalkyl, or aryl-C$_{1-6}$alkyl;
R$_{10}$a is H or C$_{1-6}$alkyl; and
R$_{11}$a is C$_{1-6}$alkyl or aryl-C$_{1-6}$alkyl
and when X$_1$ is C=O or CH$_2$ and R$_5$ is H then R$_4$ is not:

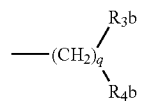

Where q is 0 to 5,
R$_3$b is H, OH or alkoxy and
R$_4$b is NH$_2$, phenyl or a C$_{3-10}$ heterocycle.

As used herein, the following definitions shall apply unless otherwise indicated.

The term "optionally substituted" means that a group may be substituted by one or more substituents which may be the same or different. When otherwise not specified, these substituents are selected from alkyl, cycloalkyl, —O—C(halogen)$_3$ preferably —OCF$_3$, biaryl, carbocyclic aryl, heterocyclic heteroaryl, acyl, amidino, amido, amino, alkyoxyamino, carbamoyl, carboxy, cyano, ether, hydroxyl, imino, halo, nitro, sulphamoyl, sulfonyl, sulphinyl, sulphenyl, sulfonamido or urea.

The term "alkyl group" as used herein, is typically a linear or branched alkyl group or moiety containing from 1 to 6 carbon atoms, preferably 2, 3, 4, or 5 carbon atoms such as a C$_{1-4}$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one two or three substituents. Suitable substituents include cyano, halogen, hydroxyl, alkylamino, dialkylamino, amido, alkylamido, dialkylamido, alkanoyl, alkoxy, sulfonamido, nitro, aryl and heteroaryl. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond. An "alkyne" moiety refers to a group consisting of at least two carbon atoms and at least one carbon-carbon triple bond.

The term "cycloalkyl" as used herein refers to mono- or bicyclic ring or ring systems consisting of 3 to 11 carbon atoms i.e. 3, 4, 5, 6, 7, 8, 9, 10 or 11 carbon atoms. The ring system may be a "saturated ring", which means that the ring does not contain any alkene or alkyne moieties. The cycloalkyl group may also be an "unsaturated ring" which means that it contains at least one alkene or alkyne moiety and the ring system is not aromatic. The cycloalkyl group may be unsubstituted or substituted as defined herein. In addition to the above mentioned substituents one or more ring carbon atoms may also be bonded via a double bond to a group selected from NH, S and O. The cycloalkyl substituent may be bonded via a linker group such as a $C_{1-6}$ alkyl group, except where the optional substituent is alkyl. One or more hydrogens of the alkyl group in the linker may be replaced by a moiety selected from the group consisting of hydroxy, halo, cyano, amino, thiol, $C_{1-6}$alkoxy, $C_{1-6}$alkylthio, $C_{1-6}$alkylamino and $C_{1-6}$ dialkylamino.

The term "aryl group" as used herein, is typically a $C_{6-10}$ aryl group such as phenyl or naphthyl. A preferred aryl group is phenyl. An aryl group may be unsubstituted or substituted at any position. Typically, it carries 1, 2, 3 or 4 substituents. Suitable substituents include cyano, halogen, hydroxyl, nitro, trifluoromethyl, alkyl, alkylthio, alkoxy, amino, alkylamino, dialkylamino, alkanoyl, amido, N-alkylamido, NN-dialkylamino, sulfonamido, aryl and heteroaryl.

The term "carbocyclic" refers to a compound which contains one or more covalently closed ring structures and the atoms forming the backbone of the ring(s) are all carbon atoms. The term thus distinguishes carbocyclic from heterocyclic rings. Carbocyclic groups include both, a "cycloalkyl group", which means a non-aromatic carbocyclic, and a "carbocyclic aryl" group, which means an aromatic carbocyclic. The carbocyclic group may optionally be substituted as defined herein.

The term "heterocyclic" or "heterocyclo" as used heroin refers to mono- or bicyclic rings or ring systems which include one or more heteroatoms selected from N, S and O. The rings or ring systems include 1 to 6 carbon atoms in addition to the heteroatom(s). The term heterocyclic group include both a "heteroalicyclic" group, which means a non-aromatic heterocycle and a "heteroaryl" group, which means an aromatic heterocycle. The heterocyclic moiety may be unsubstituted or substituted as defined herein and the substituents, when positioned adjacent to one another, may combine to form cycloaky or heteroalicyclic ring systems for example methylendioxy or difluoromethylendioxy. The heterocyclic substituent may be bonded via a carbon atom or a heteroatom. The heterocyclic group may also include the oxides of nitrogen and sulfur if nitrogen or sulfur are present in the ring.

The term "heteroaryl" as used herein refers to mono- or bicyclic ring or ring systems which include one or more heteroatoms selected from N, S and O. The rings or ring systems include 1 to 13 carbon atoms in addition to the heteroatom(s) and contain at least one aromatic ring with a heteroatom. The heteroaryl group may also include the oxides of nitrogen and sulfur if nitrogen or sulfur is present. Examples of monocyclic heteroaryl groups include, but are not limited to, furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrarinyl and triarinyl. Examples of bicyclic heterocycles include but are not limited to indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like. Examples of tricyclic heterocycles include, but are not limited to thianthrenyl, xanthenyl, phenoxathiinyl, carbazolyl, carbolinyl, phenanthridinyl, acridinyl, perimidinyl, phenanthrolinyl, phenazinyl, phenothiazinyl and phenoxazinyl. The heteroaryl group may be unsubstituted or substituted as defined herein. The substituents, when positioned adjacent to one another, may combine to form a cycloalkyl or heteroalicyclic ring for example methylendioxy and difluoromethylendioxy. The heteroaryl substituent may be bonded via a carbon atom or a heteroatom.

The term "arylalkyl", as used herein, refers to a chemical moiety of formula aryl-$C_{1-6}$alkyl or $C_{1-6}$alkyl-aryl as those terms are defined herein.

The term "heteroarylalkyl", used as herein, refers to a chemical moiety of formula heteroaryl-$C_{1-6}$alkyl or $C_{1-6}$alkyl-heteroaryl as those terms are defined herein.

The term "acyl", as used herein, refers to a chemical moiety of formula (CH$_2$)yC(=NH)NRzR'z wherein y is 1-6.

The term "amidino" refers to a chemical moiety with the formula (CH$_2$)yC(=NH)NRzR'z wherein y is 1-6.

The term "amido" refers to both, a "C-amido" group which means a chemical moiety with the formula —C(=O)NRzR'z and a "N-amido" group which means a chemical moiety with the formula —NRzC(=O)R'z.

The term "amine" or "amino" refers to a chemical moiety of formula —NRzR'z. The definition of an amine is also understood to include their N-oxides.

A "cyano" group refers to a chemical moiety of formula —CN.

The term "hydroxy" or "hydroxyl" as used herein, refers to a chemical moiety of formula —OH.

The term "halogen" or "halo" refers to an atom selected from the group consisting of fluorine, chlorine, bromine and iodine.

The term "alkanoyl", as used herein, refers to a chemical moiety with the formula —C(=O)Rz.

The term "sulfone" or "sulfonyl" refers to a chemical moiety with the formula —S(=O)$_2$Rz.

The term "sulfinyl" refers to a chemical moiety with the formula —S(=O)Rz.

The term "sulfenyl" refers to a chemical moiety with the formula —SRz.

A "sulfamoyl" group refers to a chemical moiety with the formula —NRz—S(=O)$_2$NRzR'z.

The term "sulfonamide" refers to both an "S-sulfonamido" group which moans a chemical moiety with the formula —S(=O)$_2$NRzR'z and an "N-sulfonamido" group which means a chemical moiety with the formula —N—S(=O)$_2$R'z.

The term "thiocarbonyl" refers to a chemical moiety with the formula (CH$_2$)yC(=S)Rz wherein y is 1-6.

The term "thio" or "thiol", as used herein, refers to a chemical moiety of formula —SH.

The term "thioamide" refers to both a "C-thioamido" group which means a chemical moiety with the formula (CH$_2$)yC(=S)NRzR'z and a "N-thioamido" group which means a chemical moiety with the formula (CH$_2$)yNRzC(=S)R'z wherein y is 1-6.

An "urea" group refers to a chemical moiety of formula —NRzC(=O)NRzR'z.

Rz and R'z are independently selected from the group consisting of hydrogen, $C_{1-6}$alkyl, cycloalkyl, $C_{1-6}$alkoxy, aryl-$C_{1-6}$alkyl, aryl and heteroaryl.

In a preferred embodiment;

X is C(=O).

$R_2$ is selected from $NR_{24}R_{25}$, Preferably $R_{24}$ and $R_{25}$ are the same or different and each represents hydrogen, or optionally substituted $C_{1-6}$alkyl. More preferably, $R_{24}$ and $R_{25}$ are $CH_3$.

Alternatively, $R_2$ is selected from compounds of formula (III), (IV) or (V)

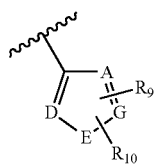

(III)

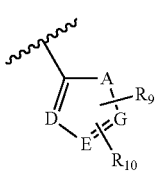

(IV)

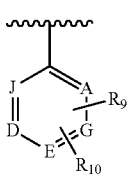

(V)

Wherein;

A, D, E, G, and J are the same or different and each represents C, or N with the proviso that in each instance at least one of A, D, E, G or J is N;

When $R_2$ is selected from compounds of formula (III), E may also represent O or S; and When $R_2$ is selected from compounds of formula (IV), A may also represent O or S; Preferred moities of formula (III), (IV) and (V) are Imidazole, Pyrazole, Pyrrole, Oxazole, Oxadiazole, Thiazole, Thiadiazole, Pyridine, Pyrimidine, Pyrazine, Pyridazine, and Triazine. More preferably $R_2$ is selected from Imidazole, Pyrazole, or Pyridine.

$R_9$ and $R_{10}$ are the same or different and each represents hydrogen, halogen, hydroxyl, nitrile, optionally substituted amino, optionally substituted acyl, optionally substituted $C_{1-3}$ alkyl, optionally substituted arylalky, optionally substituted aryl or optionally substituted heteroaryl or may be taken together to form an optionally substituted saturated or partially saturated 5-7 membered heterocyclic or carbocyclic ring. Preferably $R_9$ and $R_{10}$ are alkyl, more preferably $CH_3$.

Alternatively, $R_2$ is selected from compounds of formula (VI)

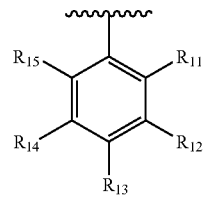

(VI)

$R_{11}$, $R_{12}$, $R_{13}$, $R_{14}$, and $R_{15}$ are the same or different and each represents hydrogen, halogen, hydroxyl, optionally substituted amino, optionally substituted acyl, optionally substituted alkyl, any of the pairs $R_{11}$ and $R_{12}$, or $R_{12}$ and $R_{13}$, or $R_{15}$ and $R_{14}$, or $R_{14}$ and $R_{15}$ or may be taken together to form an optionally substituted saturated or partially saturated 5-7 membered heterocyclic or carbocyclic ring.

Preferred moities of formula (VI) include phenyl, fluorphenyl, chlorophenyl, cyanophenyl, aminophenyl, acetamidophenyl, tetrahydrobenzofuran, benzopyran, dihydrobenzodioxin, benzoxazinone, benzooxadiazole, benzoctioxole, indoline, indole, indazole, and benzomorpholine. More preferred moities are phenyl, fluorophenyl, cyanophenyl, tetrahydrobenzofuran, benzopyran, dihydrobenzodioxin, benzoxazinone, benzooxadiazole, benzodioxole, indoline, and benzomorpholine.

Preferably $R^1$ is

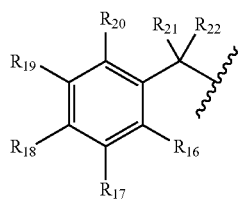

(VII)

Wherein $R_{16}$, $R_{17}$, $R_{18}$, $R_{19}$ and $R_{20}$ are the same or different and each represents hydrogen, halogen, hydroxyl, optionally substituted amino, optionally substituted acyl, nitrile, optionally substituted $C_{1-3}$ alkyl or optionally substituted alkoxy $R_{21}$ and $R_{22}$ are the same or different and each represents hydrogen, hydroxyl, and optionally substituted $C_{1-3}$ alkyl. Preferably $R_{17}$, $R_{18}$ and $R_{19}$ are the same or different and each represents H, Cl, F, or $CH_3$. More preferably, $R_{17}$, $R_{18}$ and $R_{19}$ are the same or different and each represents H or Cl.

Preferably $R_3$ is H, F or $CH_3$. More preferably $R_3$ is H or F.

$R_4$ is preferably selected from the group consisting of optionally substituted alkyl, optionally substituted cycloalkyl, optionally substituted heterocycloalkyl, substituted aryl, optionally substituted arylalkyl, and optionally substituted heteroaryl. Preferred examples include methyl, ethyl, propyl, isopropyl, butyl, tert-butyl, pentyl, cyclopropyl, cyclopropylmethyl, cyclobutyl, cyclopentyl, 2-hydroxyethyl, hydroxypropyl, hydroxybutyl, propane-1,3-diol, methoxyethyl, phenyl, benzyl, phenethyl, 3-phenylpropyl, piperidinyl, pyrolhdinyl, morpholinyl, piperazinyl, indazolyl, pyridyl, thiadiazolyl, and thiazolyl.

$R_5$ is preferably selected from hydrogen, optionally substituted alkyl, preferably $CH_3$ or $NR_4R_5$ may form an optionally substituted saturated or partially saturated 4-7 membered ring with the general formula (II). More preferably, $R_5$ is selected from hydrogen, $CH_3$ or $NR_4R_5$ may form an optionally substituted saturated or partially saturated 4-6 membered ring with the general formula (II) examples of which include pyrrolidinyl, piperazinyl, piperidinyl.

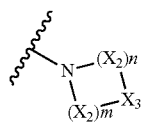

(II)

$X_2$ is C(=O), $CH_2$ or CH($R_6$) or C($R_6$)($R_6$),
$X_3$ is $CH_2$, CH($R_7$), C($R_7$)($R_7$), NH, N($R_8$), or O
Wherein;

Each $R_6$ independently represents halogen, hydroxyl, optionally substituted alkoxy, optionally substituted aryloxy, optionally substituted alkyl, optionally substituted cycloalkyl, optionally substituted arylalky, optionally substituted aryl or optionally substituted heteroaryl. More preferably, $R_6$ independently represents fluoro, hydroxyl and methyl.

Each $R_7$ independently represents halogen, hydroxyl, optionally substituted acyl, optionally substituted alkoxy, optionally substituted aryloxy, optionally substituted alkyl, optionally substituted cycloalkyl, optionally substituted arylalky, optionally substituted aryl or optionally substituted heteroaryl independently represents fluoro, hydroxyl, cyclohexylmethyl, phenyl, fluorophenyl and phenoxy.

$R_8$ is optionally substituted acyl, optionally substituted alkyl, optionally substituted cycloalkyl, optionally substituted arylalkyl, optionally substituted aryl or optionally substituted heteroaryl;

More preferred compounds are those selected from compounds of formula (VIII);

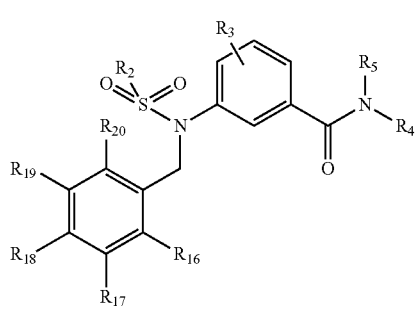

(VIII)

Wherein;
$R_2$ is selected from $NR_{24}R_{25}$ or compounds of formula (III), (IV) (V) or (VI), $R_3$, $R_4$, $R_5$, $R_{16}$, $R_{17}$, $R_{18}$, $R_{19}$ and $R_{20}$ are as defined above.

Most preferred compounds are those selected from compounds of formula (IX);

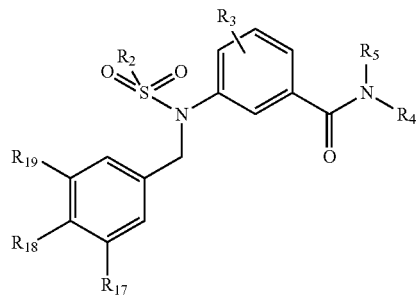

(IX)

Wherein;
$R_2$ is selected from $NR_{24}R_{25}$ or compounds of formula (III), (IV), (V) or (VI) as defined.
$R_3$, $R_4$, $R_5$, $R_{17}$, $R_{18}$, and $R_{19}$ are as defined above.
Particularly Preferred Compounds of the Invention Include:
3-[(4-Chloro-benzyl)-(1-methyl-1H-pyrazole-3-sulfonyl)-amino]-N-(2-hydroxy-ethyl)-benzamide
N-Benzyl-3-[benzyl-(1-methyl-1H-imidazole-4-sulfonyl)-amino]-benzamide
3-[Benzyl-(pyridine-3-sulfonyl)-amino]-N-isopropyl-benzamide
3-(Benzenesulfonyl-benzyl-amino)-N-(1H-indazol-6-yl)-benzamide
3-[(4-Acetylamino-benzenesulfonyl)-benzylamino]-N-isopropyl-benzamide
5-[Benzyl-(3-oxo-3,4-dihydro-2H-benzo[1,4]oxazine-6-sulfonyl)-amino]-2-fluoro-N-isopropyl-benzamide
3-[(4-Chloro-benzyl)-(2-methyl-2H-pyrazole-3-sulfonyl)-amino]-N-isopropyl-benzamide
3-(Benzenesulfonyl-benzyl-amino)-N-benzyl-benzamide
3-(Benzenesulfonyl-benzyl-amino)-N-isopropyl-benzamide
3-(Benzenesulfonyl-benzyl-amino)-N-phenethyl-benzamide
N-Benzyl-N-[3-(4-phenyl-piperidine-1-carbonyl)-phenyl]-benzenesulfonamide
N-Benzyl-N-[3-(3-phenyl-piperidine-1-carbonyl)-phenyl]-benzenesulfonamide
N-Benzyl-N-[3-(2-phenyl-morpholine-4-carbonyl)-phenyl]-benzenesulfonamide
N-Benzyl-N-[3-(4-phenoxy-piperidine-1-carbonyl)-phenyl]-benzenesulfonamide
3-(Benzenesulfonyl-benzyl-amino)-N-(3-phenyl-propyl)-benzamide
3-(Benzenesulfonyl-benzyl-amino)-N-methyl-benzimide
3-(benzenesulfonyl-benzyl-amino)-N-tert-butyl-benzamide
N-Benzyl-N-[3-(3-phenyl-carbonyl)-phenyl]-methanesulfenamide
N-Benzyl-N-[3-(2-phenyl-morpholine-4-carbonyl)-phenyl]-methanesulfonamide
N-Benzyl-N-[3-(4-phenoxy-piperidine-1-carbonyl)-phenyl]-methanesulfonamide
N-Benzyl-N-[3-(4-phenyl-piperidine-1-carbonyl)-phenyl]-methanesulfonamide 1-Methyl-1H-imidazole-4-sulfonic acid benzyl-[3-(4-phenyl-piperidine-carbonyl)-phenyl]-amide
N-Benzyl-N-[3-(morpholine-4-carbonyl)-phenyl]-benzonesulfonamide
3-(Benzenesulfonyl-benzyl-amino)-N-pyridin-2-yl)methyl-benzamide
3-(Benzenesulfonyl-benzyl-amino)-N-(1H-indazol-5-yl)-benzamide 3-(Benzenesulfonyl-benzyl-amino)-N-(4-imidazol-1-yl-phenyl)-benzamide
3-(Benzenesulfonyl-benzyl-amino)-N-(4-pyrazol-1-yl-phenyl)-benzamide
3-(Benzenesulfonyl-benzyl-amino)-N-[1,3,4]thiadiazol-2-yl-benzamide
3-(Benzenesulfonyl-benzyl-amino)-N-thiazol-2-yl-benzamide
N-[4-(Aminocarbonyl)phenyl]-3-[benzyl(phenylsulfonyl)amino]benzamide
N-[3-(Aminocarbonyl)phenyl]-3-[benzyl(phenylsulfonyl)amino]benzamide
3-(Benzenesulfonyl-benzyl-amino)-N-phenyl-benzamide
1-Methyl-1H-imidazole-4-sulfonic acid benzyl-[3-(2-phenyl-morpholine-4-carbonyl)-phenyl]-amide
3-[Benzyl-(1,2-dimethyl-1H-imidazole-4-sulfonyl)-amino]-N-isopropyl-benzamide
3-[Benzyl-(1-methyl-1H-pyrazole-3-sulfonyl)-amino]-N-isopropyl-benzamide
3-[Benzyl-(2,4-dimethyl-thiazole-5-sulfonyl)-amino]-N-isopropyl-benzamide
N-Benzyl-2-fluoro-N-[3-(morpholine-4-carbonyl)-phenyl]-benzenesulfonamide
3-[Benzyl-(2-fluoro-benzenesulfonyl)-amino]-N,N-dimethyl-benzamide
3-[Benzyl-(3-fluoro-benzenesulfonyl)-amino]-N,N-dimethyl-benzamide
N-Benzyl-4-fluoro-N-[3-(morpholine-4-carbonyl)-phenyl]-benzenesulfonamide
3-[Benzyl-(4-fluoro-benzenesulfonyl)-amino]-N,N-dimethyl-benzamide
3-[Benzyl-(4-fluoro-benzenesulfonyl)-amino]-N-isopropyl-benzamide
1-Methyl-1H-imidazole-4-sulfonic acid benzyl-{3-[4-(2-fluoro-phenyl)-piperazine-1-carbonyl]-phenyl}-amide
3-[Benzyl-(2-fluoro-benzenesulfonyl)-amino]-N-isopropyl-benzamide
3-[Benzyl-(3-fluoro-benzenesulfonyl)-amino]-N-isopropyl-benzamide
1-Methyl-1H-imidazole-4-sulfonic acid benzyl-[3-(4-cyclohexylmethyl-piperazine-1-carbonyl)-phenyl]amide
3-[Benzyl-(2,3-dihydro-benzofuran-5-sulfonyl)-amino]-N-isopropyl-benzamide
3-[Benzyl-(2,2-dimethyl-chroman-6-sulfonyl)-amino]-N-isophopyl-benzamide
3-[Benzyl-(2,3-dihydro-benzo[1,4]dioxine-6-sulfonyl)-amino]-N-isopropyl-benzamide
3-[(1-Acetyl-2,3-dihydro-1H-indole-5-sulfonyl)-benzyl-amino]-N-isopropyl-benzamide
3-[Benzyl-(2-methyl-2H-pyrazole-3-sulfonyl)-amino]-N-isopropyl-benzamide
3-[Benzyl-(4-methyl-3,4-dihydro-2H-benzo[1,4]oxazine-7-sulfonyl)-amino]-N-isopropyl-benzamide
3-[Benzyl-(3-oxo-3,4-dihydro-2H-benzo[1,4]oxazine-6-sulfonyl)-amino]-N-isopropyl-benzamide
2,3-Dihydro-benzo[1,4]dioxine-6-sulfonic acid benzyl-[3-(morpholine-4-carbonyl)-phenyl]-amide
4-Methyl-3,4-dihydro-2H-benzo[1,4]oxazine-7-sulfonic acid benzyl-[3-(morpholine-4-carbonyl)-phenyl]-amide
Benzo[1,2,5]oxadiazole-4-sulfonic acid benzyl-[3-(morpholine-4-carbanyl)-4-phenyl]-amide
Benzo[1,3]dioxole-5-sulfonic acid benzyl-[3-(morpholine-4-carbonyl)-phenyl]-amide
3-(Benzenesulfonyl-benzyl-amino)-N-cyclopropyl-benzamide
3-(Benzenesulfonyl-benzyl-amino)-N-cyclobutyl-benzamide
3-(Benzenesulfonyl-benzyl-amino)-N-cyclopentyl-benzamide
3-(Benzenesulfonyl-benzyl-amino)-N-(2-hydroxy-1,1-dimethyl-ethyl)-benzamide
3-(Benzenesulfonyl-benzyl-amino)-N-(2-hydroxy-1-methyl-ethyl)-benzamide
3-(Benzenesulfonyl-benzyl-amino)-N-(1-hydroxymethyl-propyl)-benzamide
3-(Benzenesulfonyl-benzyl-amino)-N-(2-hydroxy-propyl)-benzamide
3-(Benzenesulfonyl-benzyl-amino)-N-isobutyl-benzamide
3-(Benzenesulfonyl-benzyl)-amino)-N-ethyl-benzamide
3-(Benzenesulfonyl-benzyl-amino)-N-(2-methoxy-ethyl)-benzamide
3-(Benzenesulfonyl-benzyl-amino)-N-(2-hydroxy-ethyl)-benzamide
3-(Benzenesulfonyl-benzyl-amino)-N-propyl-benzamide
3-(Benzenesulfonyl-benzyl-amino)-N-(3-hydroxy-propyl)-benzamide
3-(Benzenesulfonyl-benzyl-amino)-N-(4-hydroxy-butyl)-benzamide
3-(Benzenesulfonyl-benzyl-amino)-N-cyclopropylmethyl-benzamide
3-(Benzenesulfonyl-benzyl-amino)-N-(2-hydroxy-1-hydroxymethyl-ethyl)-benzamide
3-(Benzenesulfonyl-benzyl-amino)-N—((R)-1-hydroxymethyl-propyl)-benzamide
5-[(Benzo[1,2,5]oxadiazole-4-sulfonyl)-benzyl-amino]-2-fluoro-N-isopropyl-benzamide
5-(Benzenesulfonyl-benzyl-amino)-2-fluoro-N-isopropyl-benzamide
5-[Benzyl-(1-methyl-1H-imidazole-4-sulfonyl)-amino]-2-fluoro-N-isopropyl-benzamide
5-[Benzyl-(4-fluoro-benzenesulfonyl)-amino]-2-fluoro-N-isopropyl-benzamide
5-[Benzyl-(2,3-dihydro-benzo[1,4]dioxine-6-sulfonyl)-amino]-2-fluoro-N-isopropyl-benzamide
5-[Benzyl-(4-cyano-benzenesulfonyl)-amino]-2-fluoro-N-isopropyl)-benzamide
5-[Benzyl-(3-cyano-benzenesulfonyl)-amino]-2-fluoro-N-isopropyl-benzamide
5-[Benzyl-(2-cyano-benzenesulfonyl)-amino]-2-fluoro-N-isopropyl-benzamide
5-[(Benzo[1,3]dioxole-5-sulfonyl)-benzyl-amino]-2-fluoro-N-isopropyl-benzamide
5-[Benzyl-(2,3-dihydro-benzofuran-5-sulfonyl)-amino]-2-fluoro-N-isopropyl-benzamide
5-[Benzyl-(pyridine-3-sulfonyl)-amino]-2-fluoro-N-isopropyl-benzamide
5-[(4-Acetylamino-benzenesulfonyl)-benzyl-amino]-2-fluoro-N-isopropyl-benzamide
3-[(4-Chloro-benzyl)-(pyridine-3-sulfonyl)-amino]-N-isopropyl-benzamide
3-[(4-Chloro-benzyl)-(3-oxo-3,4-dihydro-2H-benzo[1,4]oxazine-6-sulfonyl)-amino]-N-isopropyl-benzamide
3-[(4-Chloro-benzyl)-(1-methyl-1H-pyrazole-3-sulfonyl)-amino]-N-isopropyl-benzamide
3-[(4-Chloro-benzyl)-(1-methyl-1H-imidazole-4-sulfonyl)-amino]-N-isopropyl-benzamide 5-[Benzyl-(1-methyl-1H-pyrazole-3-sulfonyl)-amino]-2-fluoro-N-isopropyl-benzamide
3-[(4-Chloro-benzyl)-(4-methyl-3,4-dihydro-2H-benzo[1,4]oxazine-6-sulfonyl)-amino]-N-isopropyl-benzamide
3-[(4-Chloro-benzyl)-(1,2-dimethyl-1H-imidazole-4-sulfonyl)-amino]-N-isopropyl-benzamide
5-[Benzyl-(1,2-dimethyl-1H-imidazole-4-sulfonyl)amino]-2-fluoro-N-isopropyl-benzamide
5-[Benzyl-(2-methyl-2H-pyrazole-3-sulfonyl)-amino]-2-fluoro-N-isopropyl-benzamide
5-[(4-chloro-benzyl)-(pyridine-3-sulfonyl)-amino]-2-fluoro-N-isopropyl-benzamide
5-[(4-chloro-benzyl)-(1-methyl-1H-pyrazol-3-sulfonyl)-amino]-2-fluoro-N-isopropyl-benzamide
5-[(4-chloro-benzyl)-(2-methyl-2H-pyrazole-3-sulfonyl)-amino]-2-fluoro-N-isopropyl-benzamide
5-[(4-chloro-benzyl)-(1,2-dimethyl-1H-imidazole-4-sulfonyl)-amino]-2-fluoro-N-isopropyl-benzamide
5-[(4-chloro-benzyl)-(1-methyl-1H-pyrazole-4-sulfonyl)-amino]-2-fluoro-N-isopropyl-benzamide
5-[(4-Chloro-benzyl)-(3-cyano-benzenesulfonyl)-amino]-2-fluoro-N-(2-hydroxy-ethyl)-benzamide
5-[(4-Chloro-benzyl)-(3-cyano-benzenesulfonyl)-amino]-2-fluoro-N-(1-hydroxymethyl-propyl)-benzamide
N-(4-Chloro-benzyl)-3-cyano-N-[4-fluoro-3-(3-hydroxy-azetidine-carbonyl)-phenyl]-benzenesulfonamide
5-[(4-Chloro-benzyl)-(3-cyano-benzenesulfonyl)-amino]-2-fluoro-N-(2-hydroxy-1-hydroxymethyl-ethyl)-benzamide
5-[(4-Chloro-benzyl)-(3-cyano-benzenesulfonyl)-amino]-2-fluoro-N-(2-hydroxy-1-methyl-ethyl)-benzamide
5-[(4-Chloro-benzyl)-(3-cyano-benzenesulfonyl)-amino]-2-fluoro-N-(2-hydroxy-1,1-dimethyl-ethyl)-benzamide
5-[(4-Chloro-benzyl)-(3-cyano-benzenesulfonyl)-amino]-2-fluoro-N-(2-methoxy-ethyl)-benzamide
N-(4-Chloro-benzyl)-3-cyano-N-[4-fluoro-3-(3-hydroxy-piperidine-1-carbonyl)-phenyl]-benzenesulfonamide
N-(4-Chloro-benzyl)-3-cyano-N-[4-fluoro-3-((R)-3-hydroxy-pyrrolidine-1-carbonyl)-phenyl]-benzenesulfonamide
3-[(4-Chloro-benzyl)-(pyridine-3-sulfonyl)-amino]-N-(2-hydroxy-ethyl)-benzamide
3-[(4-Chloro-benzyl)-(pyridine-3-sulfonyl)-amino]-N-(2-hydroxy-1-methyl-ethyl)-benzamide
3-[(4-Chloro-benzyl)-(pyridine-3-sulfonyl)-amino]-N-(1-hydroxymethyl-propyl)-benzamide
Pyridine-3-sulfonic acid (4-chloro-benzyl)-[3-(3-hydroxy-azetidine-1-carbonyl)-phenyl]-amide
Pyridine-3-sulfonic acid (4-chloro-benzyl)-[3-(3-hydroxy-piperidine-1-carbonyl)-phenyl]-amide
3-[(4-Chloro-benzyl)-(pyridine-3-sulfonyl)-amino]-N-(2-hydroxy-1,1-dimethyl-ethyl)-benzamide
3-[(4-Chloro-benzyl)-(pyridine-3-sulfonyl)-amino]-N-(2-methoxy-ethyl)-benzamide
3-[(4-Chloro-benzyl)-(pyridine-3-sulfonyl)-amino]-N-cyclopropyl-benzamide
3-[(4-Chloro-benzyl)-(pyridine-3-sulfonyl)-amino]-N-cyclopentyl-benzamide
Pyridine-3-sulfonic acid (4-chloro-benzyl)-[3-((R)-3-fluoro-pyrrolidine-1-carbonyl)-phenyl]-amide
3-[(4-Chloro-benzyl)-(pyridine-3-sulfonyl)-amino]-N-cyclobutyl-benzamide
Pyridine-3-sulfonic acid [3-(azetidine-1-carbonyl)-phenyl]-(4-chloro-benzyl)-amide
3-[(4-Chloro-benzyl)-(1-methyl-1H-imidazole-4-sulfonyl)-amino]-N-methyl-benzamide
3-[(4-Chloro-benzyl)-(1-methyl-1H-imidazole-4-sulfonyl)-amino]-N-ethyl-benzamide
3-[(4-Chloro-benzyl)-(1-methyl-1H-imidazole-4-sulfonyl)-amino]-N-(2-methoxy-ethyl)-benzamide
3-[(4-Chloro-benzyl)-(1-methyl-1H-imidazole-4-sulfonyl)-amino]-N-cyclopropyl-benzamide
3-[(4-Chloro-benzyl)-(1-methyl-1H-imidazole-4-sulfonyl)-amino]-N-cyclopentyl-benzamide
3-[(4-Chloro-benzyl)-(1-methyl-1H-imidazole-4-sulfonyl)-amino]-N-cyclobutyl-benzamide
1-Methyl-1H-imidazole-4-sulfonic acid [3-(azetidine-1-carbonyl-phenyl]-(4-chloro-benzyl)-amide
3-[(4-Chloro-benzyl)-methyl-1H-pyrazole-3-sulfonyl)-amino]-N-methyl-benzamide
3-[(4-Chloro-benzyl)-(1-methyl-1H-pyrazole-3-sulfonyl)-amino]-N-ethyl-benzamide
3-[(4-Chloro-benzyl)-(1-methyl-11H-pyrazole-3-sulfonyl)-amino]-N-(2-methoxy-ethyl)-benzamide
3-[(4-Chloro-benzyl)-(1-methyl-1H-pyrazole-3-sulfonyl)amino]-N-cyclopropyl-benzamide
3-[(4-chloro-benzyl)-(1-methyl-1H-pyrazole-3-sulfonyl)-amino]-N-cyclobutyl-benzamide
1-Methyl-1H-pyrazole-3-sulfonic acid [3-(azetidine-1-carbonyl)-phenyl]-(4-chloro-benzyl)-amide
1-Methyl-1H-pyrazole-3-sulfonic acid (4-chloro-benzyl)-[3-(3-methyl-piperidine-1-carbonyl)-phenyl]-amide
3-[(4-Chloro-benzyl)-(1-methyl-1H-pyrazole-3-sulfonyl)-amino]-N-cyclopentyl-benzamide
3-[(4-Chloro-benzyl)-(1-methyl-1H-pyrazole-3-sulfonyl)-amino]-N-(2-hydroxy-1-methyl-ethyl)-benzamide
3-[(4-Chloro-benzyl)-(1-methyl-1H-pyrazole-3-sulfonyl)-amino]-N-(1-hydroxymethyl-propyl)-benzamide
3-[(4-Chloro-benzyl)-(1-methyl-1H-pyrazole-3-sulfonyl)-amino]-N-(2-hydroxy-1,1-dimethyl-ethyl)-benzamide
3-[(4-chloro-benzyl)-(2-methyl-2H-pyrazole-3-sulfonyl)-amino]-N-cyclobutyl-benzamide
3-[(4-chloro-benzyl)-(2-methyl-2H-pyrazole-3-sulfonyl)-amino]-N-cyclopentyl-benzamide As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromide or nitric acid and organic acids such as citric, fumaric, maleic, malic, ascorbic, succinic, tartaric, benzoic, acetic, methanesulfonic, ethanesulfonic, benzenesulfonic or p-toluenesulfonic. Pharmaceutically acceptable bases include alkali metal (e.g. sodium or potassium) and alkali earth metal (e.g. calcium or magnesium) hydroxides and organic bases such as alkyl amines, arylalkyl amines or heterocyclic amines.

The compounds of the invention may contain one or more chiral centres. For the avoidance of doubt, the chemical structures depicted herein are intended to embrace all stereo isomers of the compounds shown, including racemic and non racemic mixtures and pure enantiomers and/or diastereoisomers.

As discussed herein, the compounds of the invention are useful in the treatment of various conditions. Thus, in a second aspect, the present invention provides a compound of formula (I) as defined herein for use in medicine. Preferably the compound is used to prevent or treat conditions which require inhibition of potassium channels, such as immunological disorders, including psoriasis, rheumatoid arthritis and multiple sclerosis.

In a further aspect the present invention provides a pharmaceutical formulation comprising at least one compound of formula or as defined herein and optionally one or more excipients, carriers or diluents.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or a sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compositions of the invention can be used to treat conditions which require inhibition of potassium channels, for example in the treatment of immunological disorders and arrhythmia. Thus, in further aspects, the present invention provides:

(i) A method of treating or preventing a disorder which requires potassium channel inhibition, e.g. immunological disorders comprising administering to a subject an effective amount of at least one compound of the invention or a pharmaceutical composition of the invention, and (ii) the use of a compound of the invention in the manufacture of a medicament for use in potassium channel inhibition.

In particular, the medicament is for use in the treatment or prevention of psoriasis, rheumatoid arthritis, multiple sclerosis other immunological disorders and arrythmia.

Preferred embodiments of the first aspect apply to all other aspects mutatis mutandis.

The compounds of formula (I) may be prepared by conventional routes for example those set out in Schemes 1 to 6 shown below.

Scheme 1

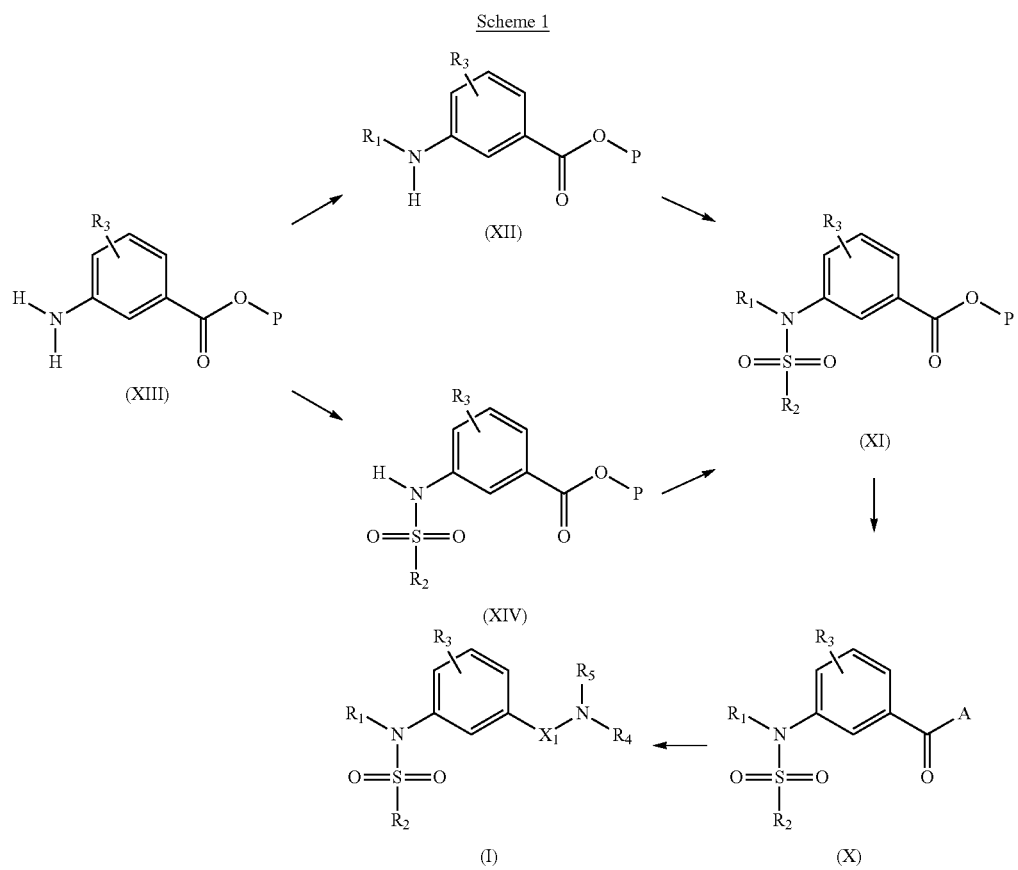

Compounds of formula (I) where $X_1$ is C=O may be prepared from compounds of formula (X) where A is OH and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile or dimethylformamide at range of temperatures from ambient to reflux temperature optionally in the presence of a activating agent such as hydroxybenzotriazole (HOBT). Alternatively, compounds of formula (I) may be prepared from compounds of formula (X) where A is Cl and amines of formula $NHR_4R_5$ in the presence of a base for example triethylamine utilising standard methods such as reaction in solvent such as tetrahydrofuran, acetonitrile or dichloromethane at range of temperatures from ambient to reflux temperature. Compounds of formula $NHR_4R_5$ are available from commercial suppliers or may be prepared by standard published methods familiar to those skilled in the art.

Compounds of formula (X) where A is OH may be prepared from compounds of formula (XI) by removal of a suitable protecting group P. In a preferred instance P is a tertiary butyl group. Removal of this protecting group may be accomplished using standard methods of acidic or basic hydrolysis or via protolytic decomposition for example treatment with trifluoroacetic acid in solvent such as tetrahydrofuran, acetonitrile, dichloromethane or toluene at a range of temperatures from ambient to reflux temperature.

Compounds of formula (XI) may be prepared, from compounds of formula (XII) and sulfonyl chlorides or sulfamoyl chlorides of formula $R_2SO_2Cl$ where $R_2$ is defined as above in the presence of a base, for example triethylamine, diisopropylamine or pyridine, utilizing standard methods such as reaction in solvent such as tetrahydrofuran, acetonitrile dichloromethane or toluene at a range of temperatures from ambient to reflux temperature. Compounds of formula $R_2SO_2Cl$ are either commercially available or may be prepared by standard published methods known to those skilled in the art.

Compounds of formula (XII) may be prepared from compounds of formula (XIII) via reductive amination of a ketone or aldehyde of formula $R_1$=O. The reaction may be performed in a one pot procedure with in situ formation and reduction of the imine or via a two stage process where the imine is isolated prior to reduction. Imine formation is performed under acid catalysis, suitable catalysts include acetic acid. Reduction may be performed using standard methods such as reaction in solvent such as tetrahydrofuran, acetonitrile, dichloromethane or toluene at a range of temperatures from ambient to reflux temperature with a suitable reductant such as sodium triacetoxyborohydride or sodium cyanoborohydride, the reduction may also be performed using catalytic hydrogenation. Compounds of formula (XIII) are either commercially available or may be prepared by standard published methods known to those skilled in the art.

Compounds of formula (XI) may also be prepared from compounds of formula (XIV) where P is a suitable protecting group, in a preferred instance a tertiary butyl group, via alkylation of the sulfonamide in a preferred instance with an alkyl bromide of formula $R_1$—Br in the presence of a base such as cesium carbonate or potassium carbonate, optionally in the presence of a phase transfer catalyst such as tetrabutylammonium bromide, utilizing standard methods such as reaction in solvent such as tetrahydrofuran, acetonitrile, dichloromethane, dimethylformamide or toluene at a range of temperatures from ambient to reflux temperature. Compounds of formula $R_1$—Br are either commercially available or may be prepared by standard published methods known to those skilled in the art.

Compounds of formula (XIV) may be prepared from compounds of formula (XIII) and sulfonyl chlorides of formula $R_2SO_2Cl$ in the presence of a base, for example triethylamine, diisopropylamine or pyridine, utilizing standard methods such as reaction in solvent such as tetrahydrofuran, acetonitrile, dichloromethane or toluene at a range of temperatures from ambient to reflux temperature. Compounds of formula $R_2SO_2Cl$ are either commercially available or may be prepared by standard published methods known to those skilled in the art.

ambient to reflux temperature. Compounds of formula $NHR_4R_5$ are either commercially available or may be prepared by standard published methods familiar to those skilled in the art.

Compounds of formula (XVII) may be prepared from compounds of formula (XII) by removal of a protecting group in a preferred instance a tertiary butyl group. This may be accomplished by standard methods of acidic or basic hydrolysis or via protolytic decomposition such as trifluoroacetic acid in solvent such as tetrahydrofuran, acetonitrile, dichloromethane or toluene at a range of temperatures from ambient to reflux temperature.

Compounds of formula (XVIII) may also be prepared from compounds of formula (XV) via reductive amination of a ketone or aldehyde of formula $R_1$=O. The reaction may be performed in a one pot procedure with in situ formation and reduction of the imine or via a two stage process where the imine is isolated and purified prior to reduction. Imine formation is performed under acid catalysis, suitable cata- Scheme 2

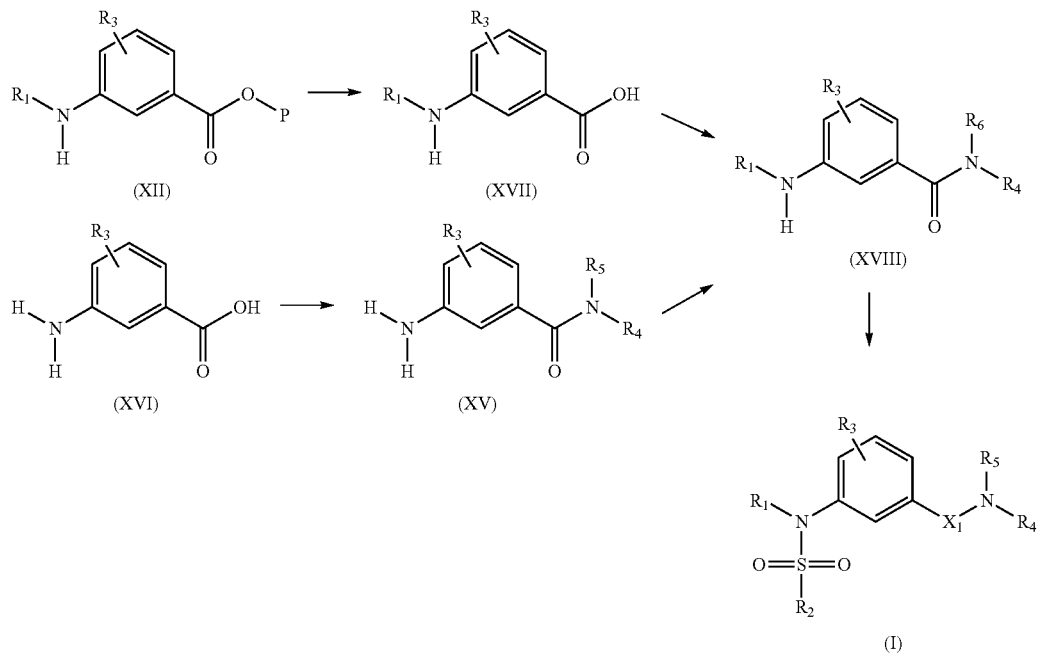

Compounds of formula (I) may also be prepared from compounds of formula (XVIII) and sulfonyl chlorides of formula $R_2SO_2Cl$ in the presence of a base, for example triethylamine, diisopropylamine or pyridine, utilizing standard methods such as reaction in solvent such as tetrahydrofuran, acetonitrile, dichloromethane or toluene at a range of temperatures from ambient to reflux temperature. Compounds of formula $R_2SO_2Cl$ are either commercially available or may be prepared by standard published methods known to those skilled in the art.

Compounds of formula (XVIII) may be prepared from the reaction of compounds of formula (XVII) and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile or dimethylformamide at range of temperatures from lysts include acetic acid. Reduction may be performed using standard methods such as reaction in solvent such as tetrahydrofuran, acetonitrile, dichloromethane or toluene at a range or temperatures from ambient to reflux temperature with a suitable reductant such as sodium triacetoxyborohydride or sodium cyanoborohydride, the reduction may also be performed using catalytic hydrogenation.

Compounds of formula (XV) may be prepared from the reaction of compounds of formula (XVI) and amines of formula $NHR_4R_5$ together with a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods such as reaction in solvent such as tetrahydrofuran, acetonitrile dimethylformamide at range of temperatures from ambient to reflux temperature. Compounds of formula $NHR_4R_5$ are either commercially available or may be prepared by standard published methods familiar to those skilled in the art. Compounds of formula (XVI) are either commercially available or may be prepared by standard published methods familiar to those in the art.

As discussed herein, the compounds of the invention are useful in the treatment of various conditions. Thus, in a second aspect, the present invention provides a compound of formula I as defined herein for use in medicine. Preferably the compound is used to prevent or treat conditions which require inhibition of potassium channels.

In a further aspect the present invention provides pharmaceutical formulation comprising at least one compound of formula I or as defined herein and optionally one or more excipients, carriers or diluents.

The compounds of the invention are found to be inhibitors of voltage gated potassium channels ($K_v$) and are therefore therapeutically useful. Such compounds are believed to be novel and the present invention also provides for these compounds. The examples which follow are illustrative and, as recognized by one skilled in the art, particular reagents or conditions could be modified as needed for individual compounds.

Many of the starting materials referred to in the reactions described above are available from commercial sources can be made by methods cited in the literature references.

EXAMPLES

The HPLC analysis was conducted using the following methods:

Solvent: [MeCN-0.05% $HCO_2H$:$H_2O$-0.1% $HCO_2H$], 10-95% gradient 3 min, 95% 2.5 min; Column: Phenomenex Gemini 50×4.6 mm i.d., C18 reverse phase; Flow rate: 0.75 mL/min unless otherwise indicated.

Solvent: [MeCN—$H_2O$/0.01% $HCO_2H$], 5-95% gradient 5 min, 95% 3 min; Column: Phertomenex Gemini 50×4.6 mm i.d., C18 reverse phase; Flow rate: 1.5 ml/min unless otherwise indicated.

Solvent: [MeCN—$H_2O$/0.1% $HCO_2H$], 5-95% gradient 3.5 min, 95% 2 min; Column: Phenomenex Gemini 50×3 mm i.d., C18 reverse phase; Flow rate: 1 mL/min unless otherwise indicated.

Solvent: [MeCN—$H_2O$/0.1% $HCO_2H$]. 5-95% gradient 6 min, 95% 3 min; Column: Phertomenex Gemini 50×4.6 mm i.d., C18 reverse phase; Flow rate: 1 mL/min unless otherwise indicated.

The preparative HPLC purification was conducted in the following manner: Solvent: [MeCN-0.5% $HCO_2H$: $H_2O$-0.1% $HCO_2H$], 5-95% gradient 12 min, 95% 3 min, Waters X-Bridge 100×19 mm i.d., C18 reverse phase; Flow rate: 16 mL/min unless otherwise indicated.

Example 1

3-[(4-Chloro-benzyl)-(1-methyl-1H-pyrazole-3-sulfonyl)-amino]-N-(2-hydroxy-ethyl)-benzamide (Method A)

i) 3-(4-Chloro-benzylamino)-benzoic acid tert-butyl ester

A solution of 3-amino-tert-butylbenzoate (2 g, 0.01 mol), 4-chlorobenzaldehyde (1.4 g. 0.01 mol) and acetic acid (0.6 ml, 0.01 mol) in dichloromethane (80 ml) was stirred for 15 min. Sodium triacetoxyborohydride (4.2 g, 0.02 mol) was then added portion-wise over 10 min. The mixture was stirred at room temperature for 16 hrs. Water (50 ml) was added and the biphasic mixture stirred for 1 hr. The organic layer was separated, washed with saturated sodium bicarbonate solution (50 ml), dried over magnesium sulfate and concentrated in vacuo. The residue was purified by column chromatography (dichloromethane/petroleum ether 80% to 100% v/v) to afford the title compound as a yellow solid (2.3 g). HPLC retention time 3.8 min. Mass spectrum (ES+) m/z 318 (M+H).

The following compounds were synthesised according to the method described using the appropriate starting materials:

5-Benzylamino-2-fluoro-N-isopropyl-benzamide

3-Benzylamino-benzoic acid tert-butyl ester

The following compounds were synthesised according to the method described using the appropriate starting materials with the exception that the reaction was performed in the absence of acetic acid.

5-(4-Chloro-benzylamino)-2-fluoro-benzoic acid tert-butyl ester

The following compounds were synthesised according to the method described using the appropriate starting materials with the exception that sodium borohydride was used as the reducing agent.

5-(4-chloro-benzylamino)-2-fluoro-N-isopropyl-benzamide ii) 3-[(4-Chloro-benzyl)-(1-methyl-1H-pyrazole-3-sulfonyl)-amino]-benzoic acid tert-butyl ester A solution of 3-(4-chloro-benzylamino)-benzoic acid tert-butyl ester (1 g, 0.03 mol), (1-Methyl-1H-Pyrazole-3-sulfonyl chloride (1.13 g, 0.06 mol) and pyridine (0.5 ml, 0.06 mol) in dichloromethane (40 ml) were refluxed for 48 hrs. On cooling, water (50 ml) was added with stirring, the organic layer was separated, dried over magnesium sulfate and concentrated in vacuo. The residue was purified by column chromatography (ethyl acetate/dichloromethane 0% to 10% v/v) to afford the title compound as a clear oil (1.33 g). Mass spectrum (ES+) m/z 49 (M+H).

The following compounds were synthesised according to the method described using the appropriate starting materials:

3-[(4-Chloro-benzyl)-(1-methyl-1H-imidazole-4-sulfonyl)-amino]-benzoic acid tert-butyl ester 3-[(4-Chloro-benzyl)-(pyridine-3-sulfonyl)-amino]-benzoic acid tert-butyl ester 5-[(4-Chloro-benzyl)-(3-cyano-benzenesulfonyl)-amino]-2-fluoro-benzoic acid tert-butyl ester 3-(Benzenesulfonyl-benzyl-amino)-benzoic acid tert-butyl ester 3-[Benzyl-(1,2-dimenthyl-1H-imidazole-4-sulfonyl)-amino]-benzoic acid tert-butyl ester 3-[Benzyl-(1-methyl-1H-pyrazole-3-sulfonyl)-amino]-benzoic acid tert-butyl ester 3-[Benzyl-(1-methyl-1H-imidazole-4-sulfonyl)-amino]-benzoic acid tert-butyl ester 3-[benzyl-(2-fluoro-benzenesulfonyl)-amino]-benzoic acid tert-butyl ester 3-[benzyl-(3-fluoro-benzenesulfonyl)-amino]-benzoic acid tert-butyl ester 3-[benzyl-(4-fluoro-benzenesulfonyl)-amino]-benzoic acid tert-butyl ester 3-(benzyl-methanesulfonyl-amino)-benzoic acid tert-butyl ester iii) 3-[(4-Chloro-benzyl)-(1-methyl-1H-pyrazole-3-sulfonyl)-amino]-benzoic acid A solution of 3-[(4-chloro-benzyl)-(1-methyl-1H-pyrazole-3-sulfonyl)-amino]-benzoic acid tert-butyl ester (1.33 g, 0.02 mol) in a mixture of trifluoroacetic acid/dichloromethane (20 ml, 1:1 v/v) was stirred for 3 hrs. The reaction mixture was concentrated to dryness in vacuo to afford the title compound as a white solid (1.37 g). HPLC retention time 2.75 Mass spectrum (ES+) m/z 405.9 (M+).

The following compounds were synthesised according to the above method described using the appropriate starting materials:
3-[(4-chloro-benzyl)-(1-methyl-1H-imidazole-4-sulfonyl)-amino]-benzoic acid
3-[(4-Chloro-benzyl)-(pyridin-3-sulfonyl)-amino]-benzoic acid
5-[(4-Chloro-benzyl)-(3-cyano-benzenesulfonyl)-amino]-2-fluoro-benzoic acid
3-(benzenesulfonyl-benzyl-amino)-benzoic acid
3-[benzyl-(2-fluoro-benzenesulfonyl)-amino]-benzoic acid
3-[benzyl-(3-fluoro-benzenesulfonyl)-amino]-benzoic acid
3-[benzyl-(4-fluoro-benzenesulfonyl)-amino]-benzoic acid The following compounds were synthesised according to the above method described using the appropriate starting materials with the following modifications:

A mixture of trifluoroacetic acid/dichloromethane (12.5 ml, 4:1 v/v) was used. On evaporation to dryness, the residue was treated with saturated sodium carbonate solution (50 ml) and partitioned with dichloromethane (50 ml). The basic aqueous solution was collected, acidified to pH 4-5 with glacial acetic acid and then extracted using ethyl acetate (2×50 ml). The organics were collected, dried over magnesium sulphate and concentrated to afford the following compounds:
3-[Benzyl-(1,2-dimethyl-1H-imidazole-4-sulfonyl)-amino]-benzoic acid
3-[Benzyl-(1-methyl-1H-pyrazole-3-sulfonyl)-amino]-benzoic acid
3-[Benzyl-(2,4-dimethyl-thiazole-5-sulfonyl)-amino]-benzoic acid
3-[Benzyl-(1-methyl-1H-imidazole-4-sulfonyl)-amino]-benzoic acid iv) 3-[(4-Chloro-benzyl)-(1-methyl-1H-pyrazole-3-sulfonyl)-amino]-N-(2-hydroxy-ethyl)-benzamide (1)

A solution of 3-[(4-chloro-benzyl)-(1-methyl-1H-pyrazole-3-sulfonyl)-amino]-benzoic acid (30 mg, 0.07 mmol), diisopropylethylamine (0.26 ml, 0.14 mmol). HATU (56 mg, 0.15 mmol) and 2-aminoethanol (9 µL, 0.14 mmol) were stirred in dry acetonitrile (3 ml) for 18 hrs. The reaction mixture was concentrated in vacuo and the residue partitioned between dichloromethane (3 ml) and water (3 ml). The organic layer was separated and dried by passage through a hydrophobic frit, then concentrated in vacuo. The crude residue was purified by preparative HPLC to afford the title compound as an off white solid (11.9 mg). HPLC retention time 5.03 min. Mass spectrum (ES+) m/z 449 (M+H).

Other compounds prepared by Method A as described for Example 1 using the appropriate starting materials are listed in TABLE 1

Example 2

N-Benzyl-3-[benzyl-(1-methyl-1H-imidazole-4-sulfonyl)-amino]-benzamide (Method B)

3-[Benzyl-(1-methyl-1H-imidazole-4-sulfonyl)-amino]-benzoic acid (50 mg, 1.3 mmol), HATU (77 mg, 0.2 mmol), diisopropylethylamine (74 µL, 0.4 mmol) and benzylamine (22 µL, 0.2 mmol) were heated in dry acetonitrile under nitrogen as 60° C. for 18 hrs. After cooling, solvent was removed in vacuo and the residue purified by preparative TLC (100% ethyl acetate), to afford the title compound as a colourless oil (4.3 mg). HPLC retention time 5.46 min. Mass spectrum (ES+) m/z 462 (M+H).

Other compounds prepared by Method B as described for Example 2 using the appropriate starting materials are listed in TABLE 1

Example 3

3-[Benzyl-(pyridine-3-sulfonyl)-amino]-N-isopropyl-benzamide i) 3-(Pyridine-3-sulfonylamino)-benzoic acid tert-butyl ester

A solution of tert-butyl-3-aminobenzoate (100 mg, 0.5 mmol) and pyridine-3-sulfonylchloride (110 mg, 0.5 mmol) in pyridine (5 ml) was heated to 50° C. for 90 min. On cooling, the reaction was diluted with toluene (100 ml) and concentrated in vacuo. This was repeated with further aliquots of toluene until all the pyridine had been removed to afford the title compound as a yellow oil (175 mg). HPLC retention time 4.27 min. Mass spectrum (ES+) m/z 335 (M+H).

ii) 3-[Benzyl-(pyridine-3-sulfonyl)amino]-benzoic acid

A solution of 3-(Pyridine-3-sulfonylamino)-benzoic acid tert-butyl ester (99 mg, 0.3 mmol), benzyl bromide (39 µL, 0.32 mmol) and Cesium Carbonate (145 mg, 0.4 mmol) in dimethylformamide (5 ml) was stirred for 16 hrs. The reaction was diluted with ethyl acetate (50 ml) and washed with water (6×100 ml). The organic layer was separated, dried over magnesium sulfate and concentrated in vacuo to give a yellow oil. The oil was dissolved in trifluoroacetic acid/dichloromethane (1:5 v/v) (10 ml), stirred for 3 hrs and then concentrated in vacuo to afford the title compound as a white solid (58.7 mg). HPLC retention time 4.31 min. Mass spectrum (APCI+) m/z 369 (M+H).

iii) 3-[Benzyl-(pyridine-3-sulfonyl)-amino]-N-isopropyl-benzamide (3)

3-[Benzyl-(pyridine-3-sulfonyl)-amino]-N-isopropyl-benzamide was prepared from 3-[benzyl-(pyridine-3-sulfonyl)-amino]-benzoic acid and isopropylamine according to the method described for Example 2. HPLC retention time 5.46 min. Mass spectrum (APCI+) m/z 410 (M+H).

Example 4

3-(Benzenesulfonyl-benzyl-amino)-N-(1H-indazol-6-yl)-benzamide (Method C)

A solution of 3-(benzenesulfonyl-benzyl-amino)-benzoic acid (25 mg, 0.068 mmol), 6-amino-1H-indazole (18 mg, 0.136 mmol), 1-(3-dimethylaminopropyl)-3-ethylcarbodiimide hydrochloride (15 mg, 0.075 mmol), mercaptobenzothiazole (2 mg, 0.007 mmol) and triethylamine (24 µl, 0.17 mmol) in dry acetonitrile (2 ml) were stirred at room temperature for 15 hrs. The reaction mixture was quenched with water (10 ml) and extracted with dichloromethane (3×7 ml). The organics were combined, dried (PTFE frit) and concentrated in vacuo. The crude residue was purified by preparative TLC (10% diethyl ether in dichloromethane) to afford the title compound as a brown solid (15 mg, 45%). HPLC retention time 5.80 min. Mass spectrum (ES+) m/z 483 (M+H).

Other compounds prepared by Method C as described for Example 4 using the appropriate starting materials are listed in TABLE 1

Example 5

3-[(4-Acetylamino-benzenesulfonyl)-benzyl-amino]-N-isopropyl-benzamide (Method D)

i) 3-Benzylamino-benzoic acid

A solution of 3-benzylamino-benzoic acid tert-butyl ester (1 g, 3 mmol) in trifluoroacetic acid/dichloromethane (1:5 v/v) (100 ml) was stirred for 16 hrs. The reaction was concentrated to dryness in vacuo to afford the title compound as a white solid. HPLC retention time 2.59 min. Mass spectrum (ES+) m/z 227.8 (M+).

The following compound was synthesised according to the above method described using the appropriate starting materials:

3-(4-Chloro-benzylamino)-benzoic acid ii) 3-Benzylamino-N-isopropyl-benzamide

A solution of 3-benzylamino-benzoic acid (500 mg, 1.5 mmol), HATU (832 mg, 2 mmol), diisopropylethylamine (0.38 ml, 2 mmol) and isopropylamine (0.19 ml, 2 mmol) in acetonitrile was heated to 50° C. for 16 hrs. On cooling, solvents were removed in vacuo and the residue partitioned between dichloromethane and water (50 ml/50 ml). The organic layer was separated, dried over magnesium sulfate and concentrated in vacuo. The residue was purified by column chromatography (ethyl acetate/dichloromethane 0% to 50% v/v) to afford the title compound as a white solid (242 mg). HPLC retention time 2.69 min. Mass spectrum (ES+) m/z 269.9 (M+H).

The following compound was synthesised according to the above method described using the appropriate starting materials:

3-(4-Chloro-benzylamino)-N-isopropyl-benzamide iii) 3-[(4-Acetylamino-benzenesulfonyl)-benzyl-amino]-N-isopropyl-benzamide (5)

3-Benzylamino-N-isopropyl-benzamide (20 mg, 0.07 mmol), pyridine (18 µL, 0.2 mmol) and 4-acetylamidobenzenesulfonyl chloride (50 mg, 0.2 mmol) were refluxed in dry dichloromethane for 18 hrs. On cooling, solvents were removed in vacuo and the residue purified by preparative LCMS to afford an off-white solid (0.5 mg). HPLC retention time 4.09 min. Mass spectrum (ES+) m/z 466 (M+H).

Other compounds prepared by Method D as described for Example 5 using the appropriate starting materials are listed in TABLE 1

Example 6

5-[Benzyl-(3-oxo-3,4-dihydro-2H-benzo[1,4]oxazine-6-sulfonyl)-amino]-2-fluoro-N-isopropyl-benzamide (Method E)

i) 5-Amino-2-fluoro-N-isopropyl-benzamide

A solution of 5-amino-2-fluorobenzoic acid (300 mg, 1.9 mmol), diisopropylethylamine (1 ml, 5.8 mmol), and isopropylamine (0.3 ml, 3.9 mmol) in acetonitrile was heated to 110° C. in microwave for 45 min. This reaction was repeated 5 times and the crude products combined then concentrated in vacuo. The residue was purified by flash chromatography (SiO₂) eluting with ethyl acetate/dichloromethane (0% to 10% v/v) to afford the title compound as a yellow solid (2.31 g). HPLC retention time 3.93 min. Mass spectrum (ES+) m/z 197 (M+H).

ii) 5-Benzylamino-2-fluoro-N-isopropyl-benzamide

5-Benzylamino-2-fluoro-N-isopropyl-benzamide was synthesized from 5-amino-2-fluoro-N-isopropyl-benzamide and benzaldehyde according to the method described in Example 1 iii) 5-[Benzyl-(3-oxo-3,4-dihydro-2H-benzo[1,4]oxazine-6-sulfonyl)-amino]-2-fluoro-N-isopropyl-benzamide (6)

A solution of 5-benzylamino-2-fluoro-N-isopropyl-benzamide (30 mg, 0.1 mmol), diisopropylethylamine (37 µL, 0.2 mmol), and 3-oxo-3,4-dihydro-2H-1,4-benzooxazine-6-sulfonyl chloride (52 mg, 0.2 mmol) was refluxed in dry dichloromethane (3 ml) for 18 hrs. On cooling, water (10 ml) was added with stirring. The organic layer was separated, dried (PTFE frit), then concentrated in vacuo. The crude residue was purified by preparative TLC (10% v/v ethyl acetate/dichloromethane) to afford the title compound as an off white solid (23 mg). HPLC retention time 7.72 min. Mass spectrum (ES+) m/z 499 (M+H).

Other compounds prepared by Method E as described for Example 6 using the appropriate starting materials are listed in TABLE 1

Example 7

3-[(4-Chloro-benzyl)-(2-methyl-2H pyrazole-3-sulfonyl)-amino]-N-isopropyl-benzamide (Method F)

3-(4-Chloro-benzylamino)-N-isopropyl-benzamide (30 mg, 0.1 mmol), diisopropylethylamine (35 µL, 0.2 mmol) and 1-methyl-1H-pyrazole-5-sulfonyl chloride (36 mg, 0.2 mmol) were stirred in dry dichloromethane (2 ml) at room temperature for 72 hrs. The reaction was diluted with dichloromethane ml) and water (5 ml) with stirring. The organics were collected, dried (PTFE frit) and concentrated in vacuo. The residue was purified by preparative TLC (10% ethyl acetate/dichloromethane) to yield the product as an off-white solid (9 mg). HPLC retention time 8.04 min. Mass spectrum (ES+) m/z 447 (M+H).

Other compounds prepared by Method F as described for Example 7 using the appropriate starting materials are listed in TABLE 1

TABLE 1

Summary of synthesis methods and characterisation data

| Example | Name | Method | LCMS Ret.n time | (ES+) m/z (M + H) |
|---|---|---|---|---|
| 1 | 3-[(Choloro-benzyl)-(1-methyl-1-H-pyrazole-3-sulfonyl)-amino]-N-(2-hydroxy-ethyl)-benzamide | A | 5.0 | 449 |
| 2 | N-Benzyl-3-[benzyl-(1-methyl-1H-imidazole-4-sulfonyl)-amino]-benzamide | B | 5.5 | 462 |
| 3 | 3-[Benzyl-(pyridine-3-sulfonyl)-amino]-N-isopropyl-benzamide | B | 5.5 | 410 |
| 4 | 3-(Benzenesulfonyl-benzyl-amino)-N-(1H-indazol-6-yl)-benzamide | C | 5.8 | 483 |
| 5 | 3-[(4-Acetylamino-benzenesulfonyl)-benzyl-amino]-N-isopropyl-benzamide | D | 4.1 | 466 |
| 6 | 5-[Benzyl-(3-oxo-3,4-dihydro-2H-benzo[1,4]oxazine-6-sulfonyl)-amino]-2-flouro-N-isopropyl-benzamide | E | 7.7 | 499 |
| 7 | 3-[(4-Chloro-benzyl)-(2-methyl-2H-pyrazole-3-sulfonyl)-amino]-N-isopropyl-benzamide | F | 8.0 | 447 |
| 8 | 3-(Benzenesulfonyl-benzyl-amino)-N-benzyl-benzamide | B | 4.7 | 457 |
| 9 | 3-(Benzenesulfonyl-benzyl-amino)-N-isopropyl-benzamide | B | 4.5 | 409 |
| 10 | 3-(Benzenesulfonyl-benzyl-amino)-N-phenethyl-benzamide | B | 4.7 | 471 |
| 11 | N-Benzyl-N-[3-(4-phenyl-piperidine-1-carbonyl)-phenyl]-benzenesulfonamide | B | 4.9 | 511 |
| 12 | N-Benzyl-N-[3-(3-phenyl-piperidine-1-carbonyl)-phenyl]-benzenesulfonamide | B | 5.0 | 511 |
| 13 | N-Benzyl-N-[3-(2-phenyl-morpholine-4-carbonyl)-phenyl]-benzenesulfonamide | B | 5.0 | 513 |
| 14 | N-Benzyl-N-[3-(4-phenoxy-piperidine-1-carbonyl)-phenyl]-benzenesulfonamide | B | 5.4 | 527 |
| 15 | 3-(Benzenesulfonyl-benzyl-amino)-N-(3-phenyl-propyl)-benzamide | B | 5.6 | 484 |
| 16 | 3-(Benzenesulfonyl-benzyl-amino)-N-methyl-benzamide | B | 4.2 | 381 |
| 17 | 3-(benzenesulfonyl-benzyl-amino)-N-tert-butyl-benzamide | C | 7.5 | 423 |
| 18 | N-benzyl-N-[3-(3-phenyl-piperidine-1-carbonyl)-phenyl]-methanesulfonamide | C | 7.1 | 449 |
| 19 | N-benzyl-N-[3-(2-phenyl-morpholine-4-carbonyl)-phenyl]-methanesulfonamide | C | 6.7 | 451 |
| 20 | N-benzyl-N-[3-(4-phenoxy-piperidine-1-carbonyl)-phenyl]-methanesulfonamide | C | 6.9 | 465 |
| 21 | N-benzyl-N-[3-(4-phenyl-piperidine-1-carbonyl)-phenyl]-methanesulfonamide | C | 7.1 | 449 |
| 22 | 1-Methyl-1H-imidazole-4-sulfonic acid benzyl-[3-(4-phenyl-piperidine-1-carbonyl)-phenyl]-amide | B | 5.9 | 515 |
| 23 | N-Benzyl-N-[3-(morpholine-4-carbonyl)-phenyl]-benzenesulfonamide | B | 5.7 | 437 |
| 24 | 3-(benzenesulfonyl-benzyl-amino)-N-pyridin-2-ylmethyl-benzamide | C | 5.6 | 445 |
| 25 | 3-(benzenesulfonyl-benzyl-amino)-N-(1H-indazol-5-yl)-benzamide | C | 5.7 | 483 |
| 26 | 3-(benzenesulfonyl-benzyl-amino)-N-(4-imidazol-1-yl-phenyl)-benzamide | C | 5.8 | 509 |
| 27 | 3-(benzenesulfonyl-benzyl-amino)-N-(4-pyrazol-1-yl-phenyl)-benzamide | C | 6.3 | 509 |
| 28 | 3-(benzenesulfonyl-benzyl-amino)-N-[1,3,4]thiadiazol-2-yl-benzamide | C | 5.7 | 451 |
| 29 | 3-(benzenesulfonyl-benzyl-amino)-N-thiazol-2-yl-benzamide | C | 6.1 | 450 |
| 30 | N-[4-(aminocarbonyl)phenyl]-3-[benzyl(phenylsulfonyl)amino]benzamide | C | 5.5 | 503 NH, salt |
| 31 | N-[3-(aminocarbonyl)phenyl]-3-[benzyl(phenylsulfonyl)amino]benzamide | C | 5.5 | 503 NH, salt |
| 32 | 3-(benzenesulfonyl-benzyl-amino)-N-phenyl-benzamide | C | 6.4 | 443 |
| 33 | 1-Methyl-1H-imidazole-4-sulfonic acid benzyl-[3-(2-phenyl-morpholine-4-carbonyl)-phenyl]-amide | B | 5.6 | 517 |
| 34 | 3-[Benzyl-(1,2-dimethyl-1H-imidazole-4-sulfonyl)-amino]-N-isopropyl-benzamide | B | 5.1 | 427 |
| 35 | 3-[Benzyl-(1-methyl-1H-pyrazole-3-sulfonyl)-amino]-N-isopropyl-benzamide | B | 5.4 | 413 |
| 36 | 3-[Benzyl-(2,4-dimethyl-thiazole-5-sulfonyl)-amino]-N-isopropyl-benzamide | B | 5.8 | 444 |
| 37 | N-benzyl-2-fluoro-N-[3-(morpholine-4-carbonyl)-phenyl]-benzenesulfonamide | C | 5.7 | 455 |
| 38 | 3-[benzyl-(2-fluoro-benzenesulfonyl)-amino]-N,N-dimethyl-benzamide | C | 5.8 | 413 |
| 39 | 3-[benzyl-(3-fluoro-benzenesulfonyl)-amino]-N,N-dimethyl-benzamide | C | 5.8 | 413 |
| 40 | N-benzyl-4-fluoro-N-[3-morpholine-4-carbonyl)-phenyl]-benzenesulfonamide | C | 5.8 | 455 |
| 41 | 3-[benzyl-(4-fluoro-benzenesulfonyl)-amino]-N,N-dimethyl-benzamide | C | 5.8 | 413 |
| 42 | 3-[benzyl-(4-fluoro-benzenesulfonyl)-amino]-N-isopropyl-benzamide | C | 8.0 | 427 |
| 43 | 1-Methyl-1H-imidazole-4-sulfonic acid benzyl-[3-[4-(2-fluoro-phenyl)-piperazine-1-carbonyl]-phenyl-amide | B | 4.1 | 534 |
| 44 | 3-[benzyl-(2-fluoro-benzenesulfonyl)-amino]-N-isopropyl-benzamide | C | 6.0 | 427 |
| 45 | 3-[benzyl-(3-fluoro-benzenesulfonyl)-amino]-N-isopropyl-benzamide | C | 6.1 | 427 |
| 46 | 1-Methyl-1H-imidazole-4-sulfonic acid benzyl-[3-(4-cyclohexylmethyl-piperazine-1-carbonyl)-phenyl]-amide | B | 2.8 | 536 |
| 47 | 3-[Benzyl-(2,3-dihydro-benzofuran-5-sulfonyl)-amino]-N-isopropyl-benzamide | D | 4.6 | 451 |
| 48 | 3-[Benzyl-(2,2-dimethyl-chroman-6-sulfonyl)-amino]-N-isopropyl-benzamide | D | 5.2 | 493 |
| 49 | 3-[Benzyl-(2,3-dihydro-benzo[1,4]dioxine-6-sulfonyl)-amino]-N-isopropyl-benzamide | D | 4.6 | 467 |
| 50 | 3-[(1-Acetyl-2,3-dihydro-1H-indole-5-sulfonyl)-benzyl-amino]-N-isopropyl-benzamide | D | 4.4 | 492 |
| 51 | 3-[Benzyl-(2-methyl-2H-pyrazole-3-sulfonyl)-amino]-N-isopropyl-benzamide | D | 4.4 | 413 |
| 52 | 3-[Benzyl-(4-methyl-3,4-dihydro-2H-benzo[1,4]oxazine-7-sulfonyl)-amino]-N-isopropyl-benzamide | D | 4.7 | 480 |
| 53 | 3-[Benzyl-(3-oxo-3,4-dihydro-2H-benzo[1,4]oxazine-6-sulfonyl)-amino]-N-isopropyl-benzamide | D | 4.3 | 480 |
| 54 | 2,3-Dihydro-benzo[1,4]dioxine-6-sulfonic acid benzyl-[3-(morpholine-4-carbonyl)-phenyl]-amide | D | 4.5 | 495 |
| 55 | 4-Methyl-3,4-dihydro-2H-benzo[1,4]oxazine-7-sulfonic acid benzyl-[3-(morpholine-4-carbonyl)-phenyl]-amide | D | 4.5 | 508 |

TABLE 1-continued

Summary of synthesis methods and characterisation data

| Example | Name | Method | LCMS Ret.n time | (ES+) m/z (M + H) |
|---|---|---|---|---|
| 56 | Benzo[1,2,5]oxadiazole-4-sulfonic acid benzyl-[3-(morpholine-4-carbonyl)-phenyl]-amide | D | 4.7 | 479 |
| 57 | Benzo[1,3]dioxole-5-sulfonic acid benzyl-[3-(morpholine-4-carbonyl)-phenyl]-amide | D | 4.7 | 481 |
| 58 | 3-(Benzenesulfonyl-benzyl-amino)-N-cyclopropyl-benzamide | B | 4.4 | 407 |
| 59 | 3-(Benzenesulfonyl-benzyl-amino)-N-cyclobutyl-benzamide | B | 4.6 | 421 |
| 60 | 3-(Benzenesulfonyl-benzyl-amino)-N-cyclopentyl-benzamide | B | 4.8 | 435 |
| 61 | 3-(Benzenesulfonyl-benzyl-amino)-N-(2-hydroxy-1,1-dimethyl-ethyl)-benzamide | B | 4.3 | 439 |
| 62 | 3-(Benzenesulfonyl-benzyl-amino)-N-(2-hydroxy-1-methyl-ethyl)-benzamide | B | 4.0 | 425 |
| 63 | 3-(Benzenesulfonyl-benzyl-amino)-N-(1-hydroxymethyl-propyl)-benzamide | B | 4.1 | 439 |
| 64 | 3-(Benzenesulfonyl-benzyl-amino)-N-(2-hydroxy-propyl)-benzamide | B | 3.9 | 425 |
| 65 | 3-(Benzenesulfonyl-benzyl-amino)-N-isobutyl-benzamide | B | 4.8 | 423 |
| 66 | 3-(Benzenesulfonyl-benzyl-amino)-N-ethyl-benzamide | B | 4.3 | 395 |
| 67 | 3-(Benzenesulfonyl-benzyl-amino)-N-(2-methoxy-ethyl)-benzamide | B | 4.2 | 425 |
| 68 | 3-(Benzenesulfonyl-benzyl-amino)-N-(2-hydroxy-ethyl)-benzamide | B | 3.8 | 411 |
| 69 | 3-(Benzenesulfonyl-benzyl-amino)-N-propyl-benzamide | B | 4.6 | 409 |
| 70 | 3-(Benzenesulfonyl-benzyl-amino)-N-(3-hydroxy-propyl)-benzamide | B | 3.9 | 425 |
| 71 | 3-(Benzenesulfonyl-benzyl-amino)-N-(4-hydroxy-butyl)-benzamide | B | 4.0 | 439 |
| 72 | 3-(Benzenesulfonyl-benzyl-amino)-N-cyclopropylmethyl-benzamide | B | 4.6 | 421 |
| 73 | 3-(Benzenesulfonyl-benzyl-amino)-N-(2-hydroxy-1-hydroxymethyl-ethyl)-benzamide | B | 3.6 | 441 |
| 74 | 3-(Benzenesulfonyl-benzyl-amino)-N-((R)-1-hydroxymethyl-propyl)-benzamide | B | 4.2 | 439 |
| 75 | 5-[(Benzo[1,2,5]oxadiazole-4-sulfonyl)-benzyl-amino]-2-fluoro-N-isopropyl-benzamide | E | 4.3 | 469 |
| 76 | 5-(Benzenesulfonyl-benzyl-amino)-2-fluoro-N-isopropyl-benzamide | E | 4.3 | 427 |
| 77 | 5-[Benzyl-(1-methyl-1H-imidazole-4-sulfonyl)-amino]-2-fluoro-N-isopropyl-benzamide | E | 7.3 | 431 |
| 78 | 5-[Benzyl-(4-fluoro-benzenesulfonyl)-amino]-2-fluoro-N-isopropyl-benzamide | E | 4.4 | 445 |
| 79 | 5-[Benzyl-(2,3-dihydro-benzo[1,4]dioxine-6-sulfonyl)-amino]-2-fluoro-N-isopropyl-benzamide | E | 4.3 | 485 |
| 80 | 5-[Benzyl-(4-cyano-benzenesulfonyl)-amino]-2-fluoro-N-isopropyl-benzamide | E | 4.3 | 452 |
| 81 | 5-[Benzyl-(3-cyano-benzenesulfonyl)-amino]-2-fluoro-N-isopropyl-benzamide | E | 4.3 | 452 |
| 82 | 5-[Benzyl-(2-cyano-benzenesulfonyl)-amino]-2-fluoro-N-isopropyl-benzamide | E | 4.2 | 452 |
| 83 | 5-[(Benzo[1,3]dioxone-5-sulfonyl)-benzyl-amino]-2-fluoro-N-isopropyl-benzamide | E | 4.3 | 471 |
| 84 | 5-[Benzyl-(2,3-dihydro-benzofuran-5-sulfonyl)-amino]-2-fluoro-N-isopropyl-benzamide | E | 4.7 | 469 |
| 85 | 5-[Benzyl-(pyridine-3-sulfonyl)-amino]-2-fluoro-N-isopropyl-benzamide | E | 3.8 | 428 |
| 86 | 5-[(4-Acetylamino-benzenesulfonyl)-benzyl-amino]-2-fluoro-N-isopropyl-benzamide | E | 3.9 | 484 |
| 87 | 3-[(4-Chloro-benzyl)-(pyridine-3-sulfonyl)-amino]-N-isopropyl-benzamide | E | 7.9 | 444 |
| 88 | 3-[(4-Chloro-benzyl)-(3-oxo-3,4-dihydro-2H-benzo[1,4]oxazine-6-sulfonyl)-amino]-N-isopropyl-benzamide | F | 7.8 | 514 |
| 89 | 3-[(4-Chloro-benzyl)-(1-methyl-1H-pyrazole-3-sulfonyl)-amino]-N-isopropyl-benzamide | E | 7.8 | 447 |
| 90 | 3-[(4-Chloro-benzyl)-(1-methyl-1H-imidazole-4-sulfonyl)-amino]-N-isopropyl-benzamide | E | 7.9 | 447 |
| 91 | 5-[Benzyl-(1-methyl-1H-pyrazole-3-sulfonyl)-amino]-2-fluoro-N-isopropyl-benzamide | E | 7.7 | 431 |
| 92 | 3-[(4-Chloro-benzyl)-(4-methyl-3,4-dihydro-2H-benzo[1,4]oxazine-6-sulfonyl)-amino]-N-isopropyl-benzamide | F | 8.4 | 514 |
| 93 | 3-[(4-Chloro-benzyl)-(1,2-dimethyl-1H-imidazole-4-sulfonyl)-amino]-N-isopropyl-benzamide | F | 7.5 | 461 |
| 94 | 5-[Benzyl-(1,2-dimethyl-1H-imidazole-4-sulfonyl)-amino]-2-fluoro-N-isopropyl-benzamide | E | 7.3 | 445 |
| 95 | 5-[Benzyl-(2-methyl-2H-pyrazole-3-sulfonyl)-amino]-2-fluoro-N-isopropyl-benzamide | E | 7.9 | 431 |
| 96 | 5-[(4-chloro-benzyl)-(pyridine-3-sulfonyl)-amino]-2-fluoro-N-isopropyl-benzamide | D | 8.1 | 464 |
| 97 | 5-[(4-chloro-benzyl)-(1-methyl-1H-pyrazole-3-sulfonyl)-amino]-2-fluoro-N-isopropyl-benzamide | D | 8.0 | 465 |
| 98 | 5-[(4-chloro-benzyl)-(2-methyl-2H-pyrazole-3-sulfonyl)-amino]-2-fluoro-N-isopropyl-benzamide | D | 8.2 | 465 |
| 99 | 5-[(4-chloro-benzyl)-(1,2-dimethyl-1H-imidazole-4-sulfonyl)-amino]-2-fluoro-N-isopropyl-benzamide | D | 7.7 | 479 |
| 100 | 5-[(4-chloro-benzyl)-(1-methyl-1H-pyrazole-4-sulfonyl)-amino]-2-fluoro-N-isopropyl-benzamide | D | 7.9 | 465 |
| 101 | 5-[(4-Chloro-benzyl)-(3-cyano-benzenesulfonyl)-amino]-2-fluoro-N-(2-hydroxy-ethyl)-benzamide | A | 7.6 | 488 |
| 102 | 5-[(4-Chloro-benzyl)-(3-cyano-benzenesulfonyl)-amino]-2-fluoro-N-(1-hydroxymethyl-propyl)-benzamide | A | 7.9 | 516 |
| 103 | N-(4-Chloro-benzyl)-3-cyano-N-[4-fluoro-3-(3-hydroxy-azetidine-1-carbonyl)-phenyl]-benzenesulfonamide | A | 7.6 | 500 |
| 104 | 5-[(4-Chloro-benzyl)-(3-cyano-benzenesulfonyl)-amino]-2-fluoro-N-(2-hydroxy-1-hydroxymethyl-ethyl)-benzamide | A | 7.4 | 518 |
| 105 | 5-[(4-Chloro-benzyl)-(3-cyano-benzenesulfonyl)-amino]-2-fluoro-N-(2-hydroxy-1-methyl-ethyl)-benzamide | A | 7.7 | 502 |
| 106 | 5-[(4-Chloro-benzyl)-(3-cyano-benzenesulfonyl)-amino]-2-fluoro-N-(2-hydroxy-1,1-dimethyl-ethyl)-benzamide | A | 8.0 | 516 |
| 107 | 5-[(4-Chloro-benzyl)-3-cyano-benzenesulfonyl)-amino]-2-fluoro-N-(2-methoxy-ethyl)-benzamide | A | 8.0 | 502 |

TABLE 1-continued

Summary of synthesis methods and characterisation data

| Example | Name | Method | LCMS Ret.n time | (ES+) m/z (M + H) |
|---|---|---|---|---|
| 108 | N-(4-Chloro-benzyl)-3-cyano-N-[4-fluoro-3-(3-hydroxy-piperidine-1-carbonyl)-phenyl]-benzenesulfonamide | A | 7.8 | 528 |
| 109 | N-(4-Chloro-benzyl)-3-cyano-N-[4-fluoro-3-((R)-3-hydroxy-pyrrolidine-1-carbonyl)-phenyl]-benzenesulfonamide | A | 7.6 | 514 |
| 110 | 3-[(4-Chloro-benzyl)-(pyridine-3-sulfonyl)-amino]-N-(2-hydroxy-ethyl)-benzamide | A | 7.0 | 446 |
| 111 | 3-[(4-Chloro-benzyl)-(pyridine-3-sulfonyl)-amino]-N-(2-hydroxy-1-methyl-ethyl)-benzamide | A | 7.1 | 460 |
| 112 | 3-[(4-Chloro-benzyl)-(pyridine-3-sulfonyl)-amino]-N-(1-hydroxymethyl-propyl)-benzamide | A | 7.4 | 474 |
| 113 | Pyridine-3-sulfonic acid (4-chloro-benzyl)-[3-(3-hydroxy-azetidine-1-carbonyl)-phenyl]-amide | A | 7.0 | 458 |
| 114 | Pyridine-3-sulfonic acid (4-chloro-benzyl)-[3-(3-hydroxy-piperidine-1-carbonyl)-phenyl]-amide | A | 7.3 | 486 |
| 115 | 3-[(4-Chloro-benzyl)-(pyridine-3-sulfonyl)-amino]-N-(2-hydroxy-1,1-dimethyl-ethyl)-benzamide | A | 7.5 | 474 |
| 116 | 3-[(4-Chloro-benzyl)-(pyridine-3-sulfonyl)-amino]-N-(2-methoxy-ethyl)-benzamide | A | 7.5 | 460 |
| 117 | 3-[(4-Chloro-benzyl)-(pyridine-3-sulfonyl)-amino]-N-cyclopropyl-benzamide | A | 7.7 | 442 |
| 118 | 3-[(4-Chloro-benzyl)-(pyridine-3-sulfonyl)-amino]-N-cyclopentyl-benzamide | A | 8.1 | 470 |
| 119 | Pyridine-3-sulfonic acid (4-chloro-benzyl)-[3-((R)-3-fluoro-pyrrolidine-1-carbonyl)-phenyl]-amide | A | 7.6 | 474 |
| 120 | 3-[(4-Chloro-benzyl)-(pyridine-3-sulfonyl)-amino]-N-cyclobutyl-benzamide | A | 8.0 | 456 |
| 121 | Pyridine-3-sulfonic acid [3-(azetidine-1-carbonyl)-phenyl]-(4-chloro-benzyl)-amide | A | 7.6 | 442 |
| 122 | 3-[(4-Chloro-benzyl)-(1-methyl-1H-imidazole-4-sulfonyl)-amino]-N-methyl-benzamide | A | 7.1 | 419 |
| 123 | 3-[(4-Chloro-benzyl)-(1-methyl-1H-imidazole-4-sulfonyl)-amino]-N-ethyl-benzamide | A | 7.3 | 433 |
| 124 | 3-[(4-Chloro-benzyl)-(1-methyl-1H-imidazole-4-sulfonyl)-amino]-N-(2-methoxy-ethyl)-benzamide | A | 7.2 | 463 |
| 125 | 3-[(4-Chloro-benzyl)-(1-methyl-1H-imidazole-4-sulfonyl)-amino]-N-cyclopropyl-benzamide | A | 7.3 | 445 |
| 126 | 3-[(4-Chloro-benzyl)-(1-methyl-1H-imidazole-4-sulfonyl)-amino]-N-cyclopentyl-benzamide | A | 7.8 | 473 |
| 127 | 3-[(4-Chloro-benzyl)-(1-methyl-1H-imidazole-4-sulfonyl)-amino]-N-cyclobutyl-benzamide | A | 8.4 | 459 |
| 128 | 1-Methyl-1H-imidazole-4-sulfonic acid [3-(azetidine-1-carbonyl)-phenyl]-(4-chloro-benzyl)-amide | A | 7.2 | 445 |
| 129 | 3-[(4-Chloro-benzyl)-(1-methyl-1H-pyrazole-3-sulfonyl)-amino]-N-methyl-benzamide | A | 5.4 | 419 |
| 130 | 3-[(4-Chloro-benzyl)-(1-methyl-1H-pyrazole-3-sulfonyl)-amino]-N-ethyl-benzamide | A | 5.6 | 433 |
| 131 | 3-[(4-Chloro-benzyl)-(1-methyl-1H-pyrazole-3-sulfonyl)-amino]-N-(2-methoxy-ethyl)-benzamide | A | 5.4 | 463 |
| 132 | 3-[(4-Chloro-benzyl)-(1-methyl-1H-pyrazole-3-sulfonyl)-amino]-N-cyclopropyl-benzamide | A | 5.6 | 445 |
| 133 | 3-[(4-Chloro-benzyl)-(1-methyl-1H-pyrazole-3-sulfonyl)-amino]-N-cyclobutyl-benzamide | A | 5.9 | 459 |
| 134 | 1-Methyl-1H-pyrazole-3-sulfonic acid [3-(azetidine-1-carbonyl)-phenyl]-(4-chloro-benzyl)-amide | A | 5.5 | 445 |
| 135 | 1-Methyl-1H-pyrazole-3-sulfonic acid (4-chloro-benzyl)-[3-(3-methyl-piperidine-1-carbonyl)-phenyl]-amide | A | 6.2 | 487 |
| 136 | 3-[(4-Chloro-benzyl)-(1-methyl-1H-pyrazole-3-sulfonyl)-amino]-N-cyclopentyl-benzamide | A | 6.0 | 473 |
| 137 | 3-[(4-Chloro-benzyl)-(1-methyl-1H-pyrazole-3-sulfonyl)-amino]-N-(2-hydroxy-1-methyl-ethyl)-benzamide | A | 5.2 | 463 |
| 138 | 3-[(4-Chloro-benzyl)-(1-methyl-1H-pyrazole-3-sulfonyl)-amino]-N-(1-hydroxymethyl-propyl)-benzamide | A | 5.3 | 477 |
| 139 | 3-[(4-Chloro-benzyl)-(1-methyl-1H-pyrazole-3-sulfonyl)-amino]-N-(2-hydroxy-1,1-dimethyl-ethyl)-benzamide | A | 5.5 | 477 |
| 140 | 3-[(4-chloro-benzyl)-(2-methyl-2H-pyrazole-3-sulfonyl)-amino]-N-cyclobutyl-benzamide | B | 6.1 | 459 |
| 141 | 3-[(4-chloro-benzyl)-(2-methyl-2H-pyrazole-3-sulfonyl)-amino]-N-cyclopentyl-benzamide | B | 9.3 | 473 |

Example 142

Kv1.3 Autopatch Electrophysiology Method

Cells stably transfected with cDNA for human Kv1.3 (in pcDNA3.1) were grown in Ex-cell 302 serum-free medium for CHO cells, supplemented with 10 μl/ml [100×] glutamine, 500 μg/ml G418 (gentimicin), and 1% HT supplement (50×, hypoxanthine and thymidine). Compounds were tested on these cells using the AutoPatch technology in whole cell mode.

The external bathing solution contained (in mM): 150 NaCl, 10 KCl, MgCl$_2$, 3 CaCl$_2$, 10 HEPES, pH 7.4 with NaOH. Patch pipettes were filled with an electrode solution of composition (in mM): 100 K-Gluconate, 20 KCl, 1 MgCl$_2$, CaCl$_2$, 10 HEPES, 11 EGTA, 5 ATP-Na$_2$, 2 Glutathione pH 7.2 with KOH.

Compounds were dissolved in DMSO (100%) and made up in the external bather at a concentration of 1 μM immediately prior to use. All experiments were conducted at room temperature.

A cell suspension (10 ml), with a density of $6 \times 10^6$ cells, was aliquoted into a 15 ml centrifuge tube and stored at 4° C. before use. Prior to use a tube was taken and centrifuged at 1000 rpm for 4 mins at room temperature. The supernatant was then discarded, leaving a cell pellet at the bottom of the tube. The pellet was then resuspended using 1 ml of cold (4° C.), filtered (0.22 μm), 0.05% BSA/bather solution (0.05 g BSA/100 ml bather). The bottom of the tube was manually agitated followed by gentle tituration. The cell suspension was then placed in the AutoPatch™ temperature controlled cell-hotel at 14° C. and regularly titurated.

A length of Teflon capillary tubing was dipped into the cell suspension solution, and a column of fluid was taken up by negative pressure. The column of fluid was in electrically connectivity with a Ag/AeCl reference electrode. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remained at the tip or in the body of the pipette. Patch pipettes typically had resistances of 2.5-3.5 MΩ. Once filled, the pipette tip and a proportion of the shaft (~15 mm) were dipped into Sigmacote (Sigma). The recording pipettes were placed in a multiwell array and mounted on the AutoPatch™ machine. Automated patch-clamping and drug-application was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a cell applicator, automated drug application system (DAS), valve controller (VFI) and a suction device all at room temperature. This equipment was completely under the control of AutoPatch.exe and operator intervention was only made when there was a requirement to refill the bather reservoirs or to prevent the loss of a cell due to a technical error.

Qualification stages prior to perfusion and drug application ensured that the observed current met the criteria for the experiment. Cells were continuously perfused with external solution at a flow rate of ~2 ml/minute. The perfusion chamber had a working volume of 80-85 μl that allowed for rapid exchange of drug solutions.

Electrophysiology voltage-step protocols and analysis of data was performed as follows. Data were sampled at 5 kHz, and filtered with a −3 dB bandwidth of 2.5 kHz. Cells were held at a voltage of −80 mV. Currents were evoked by a voltage step to +30 mV for 500 ms in duration applied every 15 s. Online analysis of the hKv1.3 current during the application of compounds was performed by the Pulse (v8.54 or v8.76, HEKA, Germany), Excel (Microsoft, USA) and AutoPatch™ software, with the total charge measured during the whole of voltage step. Inhibition of charge movement in the presence of drug was calculated relative to control.

Example 143

Summary of Kv1.3 Biological Activity

| Example | Name | hKv1.3 % Inh. |
|---|---|---|
| 1 | 3-[(4-Chloro-benzyl)-(1-methyl-1H-pyrazole-3-sulfonyl)-amino]-N-(2-hydroxy-ethyl)-benzamide | 86 |
| 2 | N-Benzyl-3-[benzyl-(1-methyl-1H-imidazole-4-sulfonyl)-amino]-benzamide | 69 |
| 3 | N-[Benzyl-(pyridine-3-sulfonyl)-amino]-N-isopropyl-benzamide | 92 |
| 4 | 3-(Benzenesulfonyl-benzyl-amino)-N-(1H-indazol-6-yl)-benzamide | 88 |
| 5 | 3-[(4-Acetylamino-benzenesulfonyl)-benzyl-amino]-N-isopropyl-benzamide | 45 |
| 6 | 5-[Benzyl-(3-oxo-3,4-dihydro-2H-benzo[1,4]oxazine-6-sulfonyl)-amino]-2-fluoro-N-isopropyl-benzamide | 84 |
| 7 | 3-[(4-Chloro-benzyl)-(2-methyl-2H-pyrazole-3-sulfonyl)-amino]-N-isopropyl-benzamide | 57 |
| 10 | 3-(Benzenesulfonyl-benzyl-amino)-N-benzyl-benzamide | 94 |
| 11 | 3-(Benzenesulfonyl-benzyl-amino)-N-isopropyl-benzamide | 89 |
| 12 | 3-(Benzenesulfonyl-benzyl-amino)-N-phenethyl-benzamide | 100 |
| 13 | N-Benzyl-N-[3-(4-phenyl-piperidine-1-carbonyl)-phenyl]-benzenesulfonamide | 97 |
| 14 | N-Benzyl-N-[3-(3-phenyl-piperidine-1-carbonyl)-phenyl]-benzenesulfonamide | 74 |
| 15 | N-Benzyl-N-[3-(2-phenyl-morpholine-4-carbonyl)-phenyl]-benzenesulfonamide | 91 |
| 16 | N-Benzyl-N-[3-(4-phenoxy-piperidine-1-carbonyl)-phenyl]-benzenesulfonamide | 97 |
| 17 | 3-(Benzenesulfonyl-benzyl-amino)-N-(3-phenyl-propyl)-benzamide | 97 |
| 18 | 3-(Benzenesulfonyl-benzyl-amino)-N-methyl-benzamide | 74 |
| 19 | 3-(benzenesulfonyl-benzyl-amino)-N-tert-butyl-benzamide | 89 |
| 20 | N-benzyl-N-[3-(3-phenyl-piperidine-1-carbonyl)-phenyl]-methanesulfonamide | 89 |
| 21 | N-benzyl-N-[3-(2-phenyl-morpholine-4-carbonyl)-phenyl]-methanesulfonamide | 47 |
| 22 | N-benzyl-N-[3-(4-phenoxy-piperidine-1-carbonyl)-phenyl]-methanesulfonamide | 63 |
| 23 | N-benzyl-N-[3-(4-phenyl-piperidine-1-carbonyl)-phenyl]-methanesulfonamide | 62 |
| 24 | 1-Methyl-1H-imidazole-4-sulfonic acid benzyl-[3-(4-phenyl-piperidine-1-carbonyl)-phenyl]-amide | 61 |
| 25 | N-Benzyl-N-[3-(morpholine-4-carbonyl)-phenyl]-benzenesulfonamide | 66 |
| 26 | 3-(benzenesulfonyl-benzyl-amino)-N-pyridin-2-ylmethyl-benzamide | 79 |
| 27 | 3-(benzenesulfonyl-benzyl-amino)-N-(1H-indazol-5-yl)-benzamide | 95 |
| 28 | 3-(benzenesulfonyl-benzyl-amino)-N-(4-imidazol-1-yl-phenyl)-benzamide | 98 |
| 29 | 3-(benzenesulfonyl-benzyl-amino)-N-(4-pyrazol-1-yl-phenyl)-benzamide | 99 |
| 30 | 3-(benzenesulfonyl-benzyl-amino)-N-[1,3,4]thiadiazol-2-yl-benzamide | 95 |
| 31 | 3-(benzenesulfonyl-benzyl-amino)-N-thiazol-2-yl-benzamide | 93 |
| 32 | N-[4-aminocarbonyl)phenyl]-3-[benzyl(phenylsulfonyl)amino]benzamide | 95 |
| 33 | N-[3-aminocarbonyl)phenyl]-3-[benzyl(phenylsulfonyl)amino]benzamide | 92 |
| 34 | 3-(benzenesulfonyl-benzyl-amino)-N-phenyl-benzamide | 91 |
| 35 | 1-Methyl-1H-imidazole-4-sulfonic acid benzyl-[3-(2-phenyl-morpholine-4-carbonyl)-phenyl]-amide | 75 |
| 36 | 3-[Benzyl-(1,2-dimethyl-1H-imidazole-4-sulfonyl)-amino]-N-isopropyl-benzamide | 88 |
| 37 | 3-[Benzyl-(1-methyl-1H-pyrazole-3-sulfonyl)-amino]-N-isopropyl-benzamide | 83 |
| 38 | 3-[Benzyl-(2,4-dimethyl-thiazole-5-sulfonyl)-amino]-N-isopropyl-benzamide | 50 |
| 39 | N-benzyl-2-fluoro-N-[3-(morpholine-4-carbonyl)-phenyl]-benzenesulfonamide | 58 |
| 40 | 3-[benzyl-(2-fluoro-benzenesulfonyl)-amino]-N,N-dimethyl-benzamide | 47 |
| 41 | 3-[benzyl-(3-fluoro-benzenesulfonyl)-amino]-N,N-dimethyl-benzamide | 41 |
| 42 | N-benzyl-4-fluoro-N-[3-(morpholine-4-carbonyl)-phenyl]-benzenesulfonamide | 61 |

| Example | Name | hKv1.3 % Inh. |
|---|---|---|
| 43 | 3-[benzyl-(4-fluoro-benzenesulfonyl)-amino]-N,N-dimethyl-benzamide | 77 |
| 44 | 3-[benzyl-(4-fluoro-benzenesulfonyl)-amino]-N-isopropyl-benzamide | 90 |
| 45 | 1-Methyl-1H-imidazole-4-sulfonic acid benzyl-(3-[4-(2-fluoro-phenyl)-piperazine-1-carbonyl]-phenyl)-amide | 53 |
| 46 | 3-[benzyl-(2-fluoro-benzenesulfonyl)-amino]-N-isopropyl-benzamide | 74 |
| 47 | 3-[benzyl-(3-fluoro-benzenesulfonyl)-amino]-N-isopropyl-benzamide | 76 |
| 48 | 1-Methyl-1H-imidazole-4-sulfonic acid benzyl-[3-(4-cyclohexylmethyl-piperazine-1-carbonyl)-phenyl]-amide | 59 |
| 49 | 3-[Benzyl-(2,3-dihydro-benzofuran-5-sulfonyl)-amino]-N-isopropyl-benzamide | 99 |
| 50 | 3-[Benzyl-(2,2-dimethyl-chroman-6-sulfonyl)-amino]-N-isopropyl-benzamide | 92 |
| 51 | 3-[Benzyl-(2,3-dihydro-benzo[1,4]dioxine-6-sulfonyl)-amino]-N-isopropyl-benzamide | 97 |
| 52 | 3-[(1-Acetyl-2,3-dihydro-1H-indole-5-sulfonyl)-benzyl-amino]-N-isopropyl-benzamide | 78 |
| 53 | 3-[Benzyl-(2-methyl-2H-pyrazole-3-sulfonyl)-amino]-N-isopropyl-benzamide | 95 |
| 54 | 3-[Benzyl-(4-methyl-3,4-dihydro-2H-benzo[1,4]oxazine-7-sulfonyl)-amino]-N-isopropyl-benzamide | 86 |
| 55 | 3-[Benzyl-(3-oxo-3,4-dihydro-2H-benzo[1,4]oxazine-6-sulfonyl)-amino]-N-isopropyl-benzamide | 71 |
| 56 | 2,3-Dihydro-benzo[1,4]dioxine-6-sulfonic acid benzyl-[3-(morpholine-4-carbonyl)-phenyl]-amide | 79 |
| 57 | 4-Methyl-3,4-dihydro-2H-benzo[1,4]oxazine-7-sulfonic acid benzyl-[3-(morpholine-4-carbonyl)-phenyl]-amide | 46 |
| 58 | Benzo[1,2,5]oxadiazole-4-sulfonic acid benzyl-[3-(morpholine-4-carbonyl)-phenyl]-amide | 41 |
| 59 | Benzo[1,3]dioxole-5-sulfonic acid benzyl-[3-(morpholine-4-carbonyl)-phenyl]-amide | 69 |
| 60 | 3-(Benzenesulfonyl-benzyl-amino)-N-cyclopropyl-benzamide | 52 |
| 61 | 3-(Benzenesulfonyl-benzyl-amino)-N-cyclobutyl-benzamide | 77 |
| 62 | 3-(Benzenesulfonyl-benzyl-amino)-N-cyclopentyl-benzamide | 86 |
| 63 | 3-(Benzenesulfonyl-benzyl-amino)-N-(2-hydroxy-1,1-dimethyl-ethyl)-benzamide | 93 |
| 64 | 3-(Benzenesulfonyl-benzyl-amino)-N-(2-hydroxy-1-methyl-ethyl)-benzamide | 54 |
| 65 | 3-(Benzenesulfonyl-benzyl-amino)-N-(1-hydroxymethyl-propyl)-benzamide | 90 |
| 66 | 3-(Benzenesulfonyl-benzyl-amino)-N-(2-hydroxy-propyl)-benzamide | 88 |
| 67 | 3-(Benzenesulfonyl-benzyl-amino)-N-isobutyl-benzamide | 89 |
| 68 | 3-(Benzenesulfonyl-benzyl-amino)-N-ethyl-benzamide | 80 |
| 69 | 3-(Benzenesulfonyl-benzyl-amino)-N-(2-methoxy-ethyl-benzamide | 82 |
| 70 | 3-(Benzenesulfonyl-benzyl-amino)-N-(2-hydroxy-ethyl)-benzamide | 81 |
| 71 | 3-(Benzenesulfonyl-benzyl-amino)-N-propyl-benzamide | 92 |
| 72 | 3-(Benzenesulfonyl-benzyl-amino)-N-(3-hydroxy-propyl)-benzamide | 78 |
| 73 | 3-(Benzenesulfonyl-benzyl-amino)-N-(4-hydroxy-butyl)-benzamide | 89 |
| 74 | 3-(Benzenesulfonyl-benzyl-amino)-N-cyclopropylmethyl-benzamide | 89 |
| 75 | 3-(Benzenesulfonyl-benzyl-amino)-N-(2-hydroxy-1-hydroxymethyl-ethyl)-benzamide | 69 |
| 76 | 3-(Benzenesulfonyl-benzyl-amino)-N-((R)-1-hydroxymethyl-propyl)-benzamide | 85 |
| 77 | 5-[(Benzo[1,2,5]oxadiazole-4-sulfonyl)-1-benzyl-amino]-2-fluoro-N-isopropyl-benzamide | 83 |
| 78 | 5-(Benzenesulfonyl-benzyl-amino)-2-fluoro-N-isopropyl-benzamide | 98 |
| 79 | 5-[Benzyl-(1-methyl-1H-imidazole-4-sulfonyl)-amino]-2-fluoro-N-isopropyl-benzamide | 58 |
| 80 | 5-[Benzyl-(4-fluoro-benzenesulfonyl)-amino]-2-fluoro-N-isopropyl-benzamide | 92 |
| 81 | 5-[Benzyl-(2,3-dihydro-benzo[1,4]dioxine-6-sulfonyl)-amino]-2-fluoro-N-isopropyl-benzamide | 92 |
| 82 | 5-[Benzyl-(4-cyano-benzenesulfonyl)-amino]-2-fluoro-N-isopropyl-benzamide | 42 |
| 83 | 5-[Benzyl-(3-cyano-benzenesulfonyl)-amino]-2-fluoro-N-isopropyl-benzamide | 100 |
| 84 | 5-[Benzyl-(2-cyano-benzenesulfonyl)-amino]-2-fluoro-N-isopropyl-benzamide | 80 |
| 85 | 5-[(Benzo[1,3]dioxole-5-sulfonyl)-benzyl-amino]-2-fluoro-N-isopropyl-benzamide | 100 |
| 86 | 5-[Benzyl-(2,3-dihydro-benzofuran-5-sulfonyl)-amino]-2-fluoro-N-isopropyl-benzamide | 97 |
| 87 | 5-[Benzyl-(pyridine-3-sulfonyl)-amino]-2-fluoro-N-isopropyl-benzamide | 91 |
| 88 | 5-[(4-Acetylamino-benzenesulfonyl)-benzyl-amino]-2-fluoro-N-isopropyl-benzamide | 52 |
| 89 | 3-[(4-Chloro-benzyl)-(pyridine-3-sulfonyl)-amino]-N-isopropyl-benzamide | 99 |
| 90 | 3-[(4-Chloro-benzyl)-(3-oxo-3,4-dihydro-2H-benzo[1,4]oxazine-6-sulfonyl)-amino]-N-isopropyl-benzamide | 80 |
| 91 | 3-[(4-Chloro-benzyl)-(1-methyl-1H-pyrazole-3-sulfonyl)-amino]-N-isopropyl-benzamide | 92 |
| 92 | 3-[(4-Chloro-benzyl)-(1-methyl-1H-imidazole-4-sulfonyl)-amino]-N-isopropyl-benzamide | 79 |
| 93 | 5-[Benzyl-(1-methyl-1H-pyrazole-3-sulfonyl)-amino]-2-fluoro-N-isopropyl-benzamide | 74 |
| 94 | 3-[(4-Chloro-benzyl)-(4-methyl-3,4-dihydro-2H-benzo[1,4]oxazine-6-sulfonyl)-amino]-N-isopropyl-benzamide | 76 |
| 95 | 3-[(4-Chloro-benzyl)-(1,2-dimethyl-1H-imidazole-4-sulfonyl)-amino]-N-isopropyl-benzamide | 94 |
| 96 | 5-[Benzyl-(1,2-dimethyl-1H-imidazole-4-sulfonyl)-amino]-2-fluoro-N-isopropyl-benzamide | 61 |
| 97 | 5-[Benzyl-(2-methyl-2H-pyrazole-3-sulfonyl)-amino]-2-fluoro-N-isopropyl-benzamide | 48 |
| 98 | 5-[(4-chloro-benzyl)-(pyridine-3-sulfonyl)-amino]-2-fluoro-N-isopropyl-benzamide | 96 |
| 99 | 5-[(4-chloro-benzyl-(1-methyl-1H-pyrazole-3-sulfonyl)-amino]-2-fluoro-N-isopropyl-benzamide | 98 |

| Example | Name | hKv1.3 % Inh. |
|---|---|---|
| 100 | 5-[(4-chloro-benzyl-(2-methyl-2H-pyrazole-3-sulfonyl)-amino]-2-fluoro-N-isopropyl-benzamide | 74 |
| 101 | 5-[(4-chloro-benzyl-(1,2-dimethyl-1H-imidazole-4-sulfonyl)-amino]-2-fluoro-N-isopropyl-benzamide | 94 |
| 102 | 5-[(4-chloro-benzyl-(1-methyl-1H-pyrazole-4-sulfonyl)-amino]-2-fluoro-N-isopropyl-benzamide | 75 |
| 103 | 5-[(4-chloro-benzyl-(3-cyano-benzenesulfonyl)-amino]-2-fluoro-N-(2-hydroxy-ethyl)-benzamide | 100 |
| 104 | 5-[(4-Chloro-benzyl-(3-cyano-benzenesulfonyl)-amino]-2-fluoro-N-(1-hydroxymethyl-propyl)-benzamide | 101 |
| 105 | N-(4-Chloro-benzyl)-3-cyano-N-[4-fluoro-3-(3-hydroxy-azetidine-1-carbonyl)-phenyl]-benzenesulfonamide | 82 |
| 106 | 5-[(4-Chloro-benzyl)-(3-cyano-benzenesulfonyl)-amino]-2-fluoro-N-(2-hydroxy-1-hydroxymethyl-ethyl)-benzamide | 94 |
| 107 | 5-[(4-Chloro-benzyl)-(3-cyano-benzenesulfonyl)-amino]-2-fluoro-N-(2-hydroxy-1-methyl-ethyl)-benzamide | 98 |
| 108 | 5-[(4-Chloro-benzyl)-(3-cyano-benzenesulfonyl)-amino]-2-fluoro-N-(2-hydroxy-1,1-dimethyl-ethyl)-benzamide | 100 |
| 109 | 5-[(4-Chloro-benzyl)-(3-cyano-benzenesulfonyl)-amino]-2-fluoro-N-(2-methoxy-ethyl)-benzamide | 100 |
| 110 | N-(4-Chloro-benzyl)-3-cyano-N-[4-fluoro-3-(3-hydroxy-piperidine-1-carbonyl)-phenyl]-benzenesulfonamide | 89 |
| 111 | N-(4-Chloro-benzyl)-3-cyano-N-[4-fluoro-3-((R)-3-hydroxy-pyrrolidine-1-carbonyl)-phenyl]-benzenesulfonamide | 53 |
| 112 | 3-[(4-Chloro-benzyl)-(pyridine-3-sulfonyl)-amino]-N-(2-hydroxy-ethyl)-benzamide | 91 |
| 113 | 3-[(4-Chloro-benzyl)-(pyridine-3-sulfonyl)-amino]-N-(2-hydroxy-1-methyl-ethyl)-benzamide | 95 |
| 114 | 3-[(4-Chloro-benzyl)-(pyridine-3-sulfonyl)-amino]-N-(1-hydroxymethyl)-propyl)-benzamide | 77 |
| 115 | Pyridine-3-sulfonic acid (4-chloro-benzyl)-[3-(3-hydroxy-azetidine-1-carbonyl)-phenyl]-amide | 50 |
| 116 | Pyridine-3-sulfonic acid (4-chloro-benzyl)-[3-(3-hydroxy-piperidine-1-carbonyl)-phenyl]-amide | 38 |
| 117 | 3-[(4-Chloro-benzyl)-(pyridine-3-sulfonyl)-amino]-N-(2-hydroxy-1,1-dimethyl-ethyl)-benzamide | 95 |
| 118 | 3-[(4-Chloro-benzyl)-(pyridine-3-sulfonyl)-amino]-N-(2-methoxy-ethyl)-benzamide | 98 |
| 119 | 3-[(4-Chloro-benzyl)-(pyridine-3-sulfonyl)-amino]-N-cyclopropyl-benzamide | 99 |
| 120 | 3-[(4-Chloro-benzyl)-(pyridine-3-sulfonyl)-amino]-N-cyclopropyl-benzamide | 96 |
| 121 | Pyridine-3-sulfonic acid (4-chloro-benzyl)-[3-((R)-3-fluoro-pyrrolidine-1-carbonyl)-phenyl]-amide | 45 |
| 122 | 3-[(4-Chloro-benzyl)-(pyridine-3-sulfonyl)-amino]-N-cyclobutyl-benzamide | 100 |
| 123 | Pyridine-3-sulfonic acid [3-azetidine-1-carbonyl)-phenyl]-(4-chloro-benzyl)-amide | 75 |
| 124 | 3-[(4-Chloro-benzyl)-(1-methyl-1H-imidazole-4-sulfonyl)-amino]-N-methyl-benzamide | 73 |
| 125 | 3-[(4-Chloro-benzyl)-(1-methyl-1H-imidazole-4-sulfonyl)-amino]-N-ethyl-benzamide | 93 |
| 126 | 3-[(4-Chloro-benzyl)-(1-methyl-1H-imidazole-4-sulfonyl)-amino]-N-(2-methoxy-ethyl)-benzamide | 66 |
| 127 | 3-[(4-Chloro-benzyl)-(1-methyl-1H-imidazole-4-sulfonyl)-amino]-N-cyclopropyl-benzamide | 95 |
| 128 | 3-[(4-Chloro-benzyl)-(1-methyl-1H-imidazole-4-sulfonyl)-amino]-N-cyclopentyl-benzamide | 93 |
| 129 | 3-[(4-Chloro-benzyl)-(1-methyl-1H-imidazole-4-sulfonyl)-amino]-N-cyclobutyl-benzamide | 96 |
| 130 | 1-Methyl-1H-imidazole-4-sulfonic acid [3-(azetidine-1-carbonyl)-phenyl]-(4-chloro-benzyl)-amide | 56 |
| 131 | 3-[(4-Chloro-benzyl)-(1-methyl-1H-pyrazole-3-sulfonyl)-amino]-N-methyl-benzamide | 99 |
| 132 | 3-[(4-Chloro-benzyl)-(1-methyl-1H-pyrazole-3-sulfonyl)-amino]-N-ethyl-benzamide | 100 |
| 133 | 3-[(4-Chloro-benzyl)-(1-methyl-1H-pyrazole-3-sulfonyl)-amino]-N-(2-methoxy-ethyl)-benzamide | 98 |
| 134 | 3-[(4-Chloro-benzyl)-(1-methyl-1H-pyrazole-3-sulfonyl)-amino]-N-cyclopropyl-benzamide | 93 |
| 135 | 3-[(4-Chloro-benzyl)-(1-methyl-1H-pyrazole-3-sulfonyl)-amino]-N-cyclobutyl-benzamide | 99 |
| 136 | 1-Methyl-1H-pyrazole-3-sulfonic acid [3-(azetidine-1-carbonyl)-phenyl]-(4-chloro-benzyl)-amide | 74 |
| 137 | 1-Methyl-1H-pyrazole-3-sulfonic acid (4-chloro-benzyl)-[3-(3-methyl-piperidine-1-carbonyl)-phenyl]-amide | 84 |
| 138 | 3-[(4-Chloro-benzyl)-(1-methyl-1H-pyrazole-3-sulfonyl)-amino]-N-cyclopentyl-benzamide | 100 |
| 139 | 3-[(4-Chloro-benzyl)-(1-methyl-1H-pyrazole-3-sulfonyl)-amino]-N-(2-hydroxy-1-methyl-ethyl)-benzamide | 82 |
| 140 | 3-[(4-Chloro-benzyl)-(1-methyl-1H-pyrazole-3-sulfonyl)-amino]-N-(1-hydroxymethyl-propyl)-benzamide | 97 |
| 141 | 3-[(4-Chloro-benzyl)-(1-methyl-1H-pyrazole-3-sulfonyl)-amino]-N-(2-hydroxy-1,1-dimethyl-ethyl)-benzamide | 100 |
| 139 | 3-[(4-chloro-benzyl)-(2-methyl-2H-pyrazole-3-sulfonyl)-amino]-N-cyclobutyl-benzamide | 47 |
| 140 | 3-[(4-chloro-benzyl)-(2-methyl-2H-pyrazole-3-sulfonyl)-amino]-N-cyclopentyl-benzamide | 87 |

Example 144

Kv1.5 Autopatch Electraphysiogogy Method

The external bathing solution contained (in mM): 150 NaCl, 10 KCl, 100 Potassium Gluconate, 3 MgCl$_2$, 1 CaCl$_2$, 10 HEPES, pH 7.4. Patch pipettes were filled with an electrode solution of composition (in mM): 160 KCl, 0.5 MgCl$_2$, 10 HEPES, 1 EGTA, pH 7.4 with KOH.

Compounds were dissolved in DMSO (100%) and made up in the external bather at a concentration of 1 µM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at mom temperature. 9.5 ml supernatant was thence discarded, leaving a cell pellet a the bottom of the tube. The pellet was then resuspended using 100 µl of cold (4° C.), filtered (0.22 µm), 0.2% BSA/bather solution (0.02 g BSA/10 ml bather). The bottom of the tube was manually agitated gently until the solution became cloudy with cells. The 100 µl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™.

Borosilicate glass patch pipettes (from 1.5 mm OD, thin-walled filamented, GC150-TF capillary glass, Harvard) were pulled using a DMZ pipette puller (Zeitz instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 amplifier (HEKA, Germany) under control of Pulse software (v8.54, HEKA, Germany), a motion controller with 2 translators (Newport, UK), valve controller (VFI) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an $R_{series}$ greater than 18 MΩ were discounted from the experiment.

Qualification stages prior to perfusion and drug application ensured that the observed current met the criteria for the experiment. Only those cells with an $1_K$>500 pA were used for experiments. Cells were continuously perfused with external solution at a flow rate of 1.8-2 ml/minute. The perfusion chamber had a working volume of 80-85 µl and allowed for rapid exchange of drug solutions. Online analysis of the $hK_v1.5$ current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz and filtered with a −3 dB bandwidth of 2.5 kHz. Cells were held at a voltage of −80 MV. Currents were evoked to a voltage step for 1000 ms in duration at 0 mV every 5 s. Currents were analysed using Pulsefit software (v8.54, HEKA, Germany), with the total charge measured during the whole of the voltage step. All other plots were produced using Igor Pro (WaveMetrics)

Example 145

Summary of Kv1.5 Biological Activity

| Example | Name | hKv1.5 % Inh. |
|---|---|---|
| 1 | 3-[(4-Chloro-benzyl)-(1-methyl-1H-pyrazole-3-sulfonyl)-amino]-N-(2-hydroxy-ethyl)-benzamide | 48 |
| 2 | N-Benzyl-3-[benzyl-(1-methyl-1H-imidazole-4-sulfonyl)-amino]-benzamide | 16 |
| 3 | 3-[Benzyl-(pyridine-3-sulfonyl)-amino]-N-isopropyl-benzamide | 52 |
| 4 | 3-[Benzesulfonyl-benzyl-amino)-N-(1H-indazole-6-yl)-benzamide | 99 |
| 5 | 3-[(4-Acetylamino-benzenesulfonyl)-benzyl-amino]-N-isopropyl-benzamide | 18 |
| 6 | 5-[Benzyl-(3-oxo-3,4-dihydro-2H-benzo[1,4]oxazine-6-sulfonyl)-amino]-2-fluoro-N-isopropyl-benzamide | 46 |
| 7 | 3-[(4-Chloro-benzyl)-(2-methyl-2H-pyrazole-3-sulfonyl)-amino]-N-isopropyl-benzamide | 54 |
| 10 | 3-(Benzenesulfonyl-benzyl-amino)-N-benzyl-benzamide | 83 |
| 11 | 3-(Benzenesulfonyl-benzyl-amino)-N-isopropyl-benzamide | 61 |
| 12 | 3-(Benzenesulfonyl-benzyl-amino)-N-phenethyl-benzamide | 98 |
| 13 | N-Benzyl-N-[3-(4-phenyl-piperidine-1-carbonyl)-phenyl]-benzenesulfonamide | 94 |
| 14 | N-Benzyl-N-[3-(3-phenyl-piperidine-1-carbonyl)-phenyl]-benzenesulfonamide | 81 |
| 15 | N-Benzyl-N-[3-(2-phenyl-morpholine-4-carbonyl)-phenyl]-benzenesulfonamide | 64 |
| 16 | N-Benzyl-N-[3-(4-phenoxy-piperidine-1-carbonyl)-phenyl]-benzenesulfonamide | 86 |
| 17 | 3-(Benzenesulfonyl-benzyl-amino)-N-(3-phenyl-propyl)-benzamide | 92 |
| 18 | 3-(Benzenesulfonyl-benzyl-amino)-N-methyl-benzamide | 20 |
| 19 | 3-(benzenesulfonyl-benzyl-amino)-N-tert-butyl-benzamide | 67 |
| 20 | N-benzyl-N-[3-(3-phenyl-piperidine-1-carbonyl)-phenyl]-methanesulfonamide | 46 |
| 21 | N-benzyl-N-[3-(2-phenyl-morpholine-4-carbonyl)-phenyl]-methanesulfonamide | 16 |
| 22 | N-benzyl-N-[3-(4-phenoxy-piperidine-1-carbonyl)-phenyl]-methanesulfonamide | 15 |
| 23 | N-benzyl-N-[3-(4-phenyl-piperidine-1-carbonyl)-phenyl]-methanesulfonamide | 13 |
| 24 | 1-Methyl-1H-imidazole-4-sulfonic acid benzyl-[3-(4-phenyl-piperidine-1-carbonyl)-phenyl]-amide | 13 |
| 25 | N-benzyl-N-[3-(morpholine-4-carbonyl)-phenyl]-benzenesulfonamide | 19 |
| 26 | 3-(benzenesulfonyl-benzyl-amino)-N-pyridin-2-ylmethyl-benzamide | 88 |
| 27 | 3-(benzenesulfonyl-benzyl-amino)-N-(1H-indazol-5-yl)-benzamide | 81 |
| 28 | 3-(benzenesulfonyl-benzyl-amino)-N-(4-imidazol-1-yl-phenyl)-benzamide | 98 |
| 29 | 3-(benzenesulfonyl-benzyl-amino)-N-(4-pyrazol-1-yl-phenyl)-benzamide | 98 |
| 30 | 3-(benzenesulfonyl-benzyl-amino)-N-[1,3,4]thiadiazol-2-yl-benzamide | 86 |
| 31 | 3-(benzenesulfonyl-benzyl-amino)-N-thiazol-2-yl-benzamide | 95 |
| 32 | N-[4-(aminocarbonyl)phenyl]-3-[benzyl(phenylsulfonyl)amino]benzamide | 86 |
| 33 | N-[3-(aminocarbonyl)phenyl]-3-[benzyl(phenylsulfonyl)amino]benzamide | 85 |
| 34 | 3-(benzenesulfonyl-benzyl-amino)-N-phenyl-benzamide | 84 |

| Example | Name | hKv1.5 % Inh. |
|---|---|---|
| 35 | 1-Methyl-1H-imidazole-4-sulfonic acid benzyl-[3-(2-phenyl-morpholine-4-carbonyl)-phenyl]-amide | 16 |
| 36 | 3-[Benzyl-(1,2-dimethyl-1H-imidazole-4-sulfonyl)-amino-N-isopropyl-benzamide | 20 |
| 37 | 3-[Benzyl-(1-methyl-1H-pyrazole-3-sulfonyl)-amino]-N-isopropyl-benzamide | 21 |
| 38 | 3-[Benzyl-(2,4-dimethyl-thiazole-5-sulfonyl)-amino]-N-isopropyl-benzamide | 10 |
| 39 | N-benzyl-2-fluoro-N-[3-(morpholine-4-carbonyl)-phenyl]-benzenesulfonamide | 12 |
| 40 | 3-[benzyl-(2-fluoro-benzenesulfonyl)-amino]-N,N-dimethyl-benzamide | 16 |
| 41 | 3-[benzyl-(3-fluoro-benzenesulfonyl)-amino]-N,N-dimethyl-benzamide | 7 |
| 42 | N-benzyl-4-fluoro-N-[3-(morpholine-4-carbonyl)-phenyl]-benzenesulfonamide | 30 |
| 43 | 3-[benzyl-(4-fluoro-benzenesulfonyl)-amino]-N,N-dimethyl-benzamide | 31 |
| 44 | 3-[benzyl-(4-fluoro-benzenesulfonyl)-amino]-N-isopropyl-benzamide | 65 |
| 45 | 1-Methyl-1H-imidazole-4-sulfonic acid benzyl-[3-[4-(2-fluoro-phenyl)-piperazine-1-carbonyl)-phenyl]-amide | 30 |
| 46 | 3-[benzyl-(2-fluoro-benzenesulfonyl)-amino]-N-isopropyl-benzamide | 12 |
| 47 | 3-[benzyl-(3-fluoro-benzenesulfonyl)-amino]-N-isopropyl-benzamide | 44 |
| 48 | 1-Methyl-1H-imidazole-4-sulfonic acid benzyl-[3-(4-cyclohexylmethyl)-piperazine-1-carbonyl)-phenyl]-amide | 10 |
| 49 | 3-[Benzyl-(2,3-dihydro-benzofuran-5-sulfonyl)-amino]-N-isopropyl-benzamide | 98 |
| 50 | 3-[Benzyl-(2,2-dimethyl-chroman-6-sulfonyl)-amino]-N-isopropyl-benzamide | 85 |
| 51 | 3-[Benzyl-(2,3-dihydro-benzo[1,4]dioxine-6-sulfonyl)-amino]-N-isopropyl-benzamide | 98 |
| 52 | 3-[(1-Acetyl-2,3-dihydro-1H-indole-5-sulfonyl)-benzyl-amino]-N-isopropyl-benzamide | 38 |
| 53 | 3-[Benzyl-(2-methyl-2H-pyrazole-3-sulfonyl)-amino]-N-isopropyl-benzamide | 83 |
| 54 | 3-[Benzyl-(4-methyl-3,4-dihydro-2H-benzo[1,4]oxazine-7-sulfonyl)-amino]-N-isopropyl-benzamide | 80 |
| 55 | 3-[Benzyl-(3-oxo-3,4-dihydro-2H-benzo[1,4]oxazine-6-sulfonyl)-amino]-N-isopropyl-benzamide | 48 |
| 56 | 2,3-Dihydro-benzo[1,4]dioxine-6-sulfonic acid benzyl-[3-(morpholine-4-carbonyl)-phenyl]-amide | 37 |
| 57 | 4-Methyl-3,4-dihydro-2H-benzo[1,4]oxazine-7-sulfonic acid benzyl-[3-(morpholine-4-carbonyl)-phenyl]-amide | 18 |
| 58 | Benzo[1,2,5]oxadiazole-4-sulfonic acid benzyl-[3-(morpholine-4-carbonyl)-phenyl]-amide | 25 |
| 59 | Benzo[1,3]dioxole-5-sulfonic acid benzyl-[3-(morpholine-4-carbonyl)-phenyl]-amide | 41 |
| 60 | 3-[Benzenesulfonyl-benzyl-amino)-N-cyclopropyl-benzamide | 54 |
| 61 | 3-[Benzenesulfonyl-benzyl-amino)-N-cyclobutyl-benzamide | 82 |
| 62 | 3-[Benzenesulfonyl-benzyl-amino)-N-cyclopentyl-benzamide | 92 |
| 63 | 3-[Benzenesulfonyl-benzyl-amino)-N-(2-hydroxy-1,1-dimethyl-ethyl)-benzamide | 86 |
| 64 | 3-[Benzenesulfonyl-benzyl-amino)-N-(2-hydroxy-1-methyl-ethyl)-benzamide | 83 |
| 65 | 3-[Benzenesulfonyl-benzyl-amino)-N-(1-hydroxymethyl-propyl)-benzamide | 47 |
| 66 | 3-[Benzenesulfonyl-benzyl-amino)-N-(2-hydroxy-propyl)-benzamide | 47 |
| 67 | 3-[Benzenesulfonyl-benzyl-amino)-N-isobutyl-benzamide | 78 |
| 68 | 3-[Benzenesulfonyl-benzyl-amino)-N-ethyl-benzamide | 43 |
| 69 | 3-[Benzenesulfonyl-benzyl-amino)-N-(2-methoxy-ethyl)-benzamide | 43 |
| 70 | 3-[Benzenesulfonyl-benzyl-amino)-N-(2-hydroxy-ethyl)-benzamide | 38 |
| 71 | 3-[Benzenesulfonyl-benzyl-amino)-N-propyl-benzamide | 75 |
| 72 | 3-[Benzenesulfonyl-benzyl-amino)-N-(3-hydroxy-propyl)-benzamide | 57 |
| 73 | 3-[Benzenesulfonyl-benzyl-amino)-N-(4-hydroxy-butyl)-benzamide | 45 |
| 74 | 3-[Benzenesulfonyl-benzyl-amino)-N-cyclopropylmethyl-benzamide | 79 |
| 75 | 3-[Benzenesulfonyl-benzyl-amino)-N-(2-hydroxy-1-hydroxymethyl-ethyl)-benzamide | 37 |
| 76 | 3-[Benzenesulfonyl-benzyl-amino)-N-((R)-1-hydroxymethyl-propyl)-benzamide | 72 |
| 77 | 5-[(Benzo[1,2,5]oxadiazole-4-sulfonyl)-benzyl-amino]-2-fluoro-N-isopropyl-benzamide | 73 |
| 78 | 5-(Benzenesulfonyl-benzyl-amino)-2-fluoro-N-isopropyl-benzamide | 74 |
| 79 | 5-[Benzyl-(1-methyl-1H-imidazole-4-sulfonyl)-amino]-2-fluoro-N-isopropyl-benzamide | 13 |
| 80 | 5-[Benzyl-(4-fluoro-benzenesulfonyl)-amino]-2-fluoro-N-isopropyl-benzamide | 94 |
| 81 | 5-[Benzyl-(2,3-dihydro-benzo[1,4]dioxine-6-sulfonyl)-amino]-2-fluoro-N-isopropyl-benzamide | 78 |
| 82 | 5-[Benzyl-(4-cyano-benzenesulfonyl)-amino]-2-fluoro-N-isopropyl-benzamide | 46 |
| 83 | 5-[Benzyl-(3-cyano-benzenesulfonyl)-amino]-2-fluoro-N-isopropyl-benzamide | 96 |
| 84 | 5-[Benzyl-(2-cyano-benzenesulfonyl)-amino]-2-fluoro-N-isopropyl-benzamide | 58 |
| 85 | 5-[(Benzo[1,3]dioxole-5-sulfonyl)-benzyl-amino]-2-fluoro-N-isopropyl-benzamide | 89 |
| 86 | 5-[Benzyl-(2,3-dihydro-benzofuran-5-sulfonyl-amino]-2-fluoro-N-isopropyl-benzamide | 78 |
| 87 | 5-[(Benzyl-(pyridine-3-sulfonyl)-amino]-2-fluoro-N-isopropyl-benzamide | 75 |
| 88 | 5-[(4-Acetylamino-benzenesulfonyl)-benzyl-amino]-2-fluoro-N-isopropyl-benzamide | 45 |
| 89 | 3-[(4-Chloro-benzyl)-(pyridine-3-sulfonyl)-amino]-N-isopropyl-benzamide | 87 |
| 90 | 3-[(4-Chloro-benzyl)-(3-oxo-3,4-dihydro-2H-benzo[1,4]oxazine-6-sulfonyl)-amino]-N-isopropyl-benzamide | 69 |
| 91 | 3-[(4-Chloro-benzyl)-(1-methyl-1H-pyrazole-3-sulfonyl)-amino]-N-isopropyl-benzamide | 92 |

| Example | Name | hKv1.5 % Inh. |
|---|---|---|
| 92 | 3-[(4-Chloro-benzyl)-(1-methyl-1H-imidazole-4-sulfonyl)-amino]-N-isopropyl-benzamide | 40 |
| 93 | 5-[Benzyl-(1-methyl-1H-pyrazole-3-sulfonyl)-amino]-2-fluoro-N-isopropyl-benzamide | 28 |
| 94 | 3-[(4-Chloro-benzyl)-(4-methyl-3,4-dihydro-2H-benzo[1,4]oxazine-6-sulfonyl)-amino]-N-isopropyl-benzamide | 82 |
| 95 | 3-[(4-Chloro-benzyl)-(1,2-dimethyl-1H-imidazole-4-sulfonyl)-amino]-N-isopropyl-benzamide | 83 |
| 96 | 5-[(Benzyl-(1,2-dimethyl-1H-imidazole-4-sulfonyl)-amino]-2-fluoro-N-isopropyl-benzamide | 21 |
| 97 | 5-[(Benzyl-(2-methyl-2H-pyrazole-3-sulfonyl)-amino]-2-fluoro-N-isopropyl-benzamide | 17 |
| 98 | 5-[(4-chloro-benzyl)-(pyridine-3-sulfonyl)-amino]-2-fluoro-N-isopropyl-benzamide | 84 |
| 99 | 5-[(4-chloro-benzyl)-(1-methyl-1H-pyrazole-3-sulfonyl)-amino]-2-fluoro-N-isopropyl-benzamide | 87 |
| 100 | 5-[(4-chloro-benzyl)-(2-methyl-2H-pyrazole-3-sulfonyl)-amino]-2-fluoro-N-isopropyl-benzamide | 46 |
| 101 | 5-[(4-chloro-benzyl)-(1,2-dimethyl-1H-imidazole-4-sulfonyl)-amino]-2-fluoro-N-isopropyl-benzamide | 38 |
| 102 | 5-[(4-chloro-benzyl)-(1-methyl-1H-pyrazole-4-sulfonyl)-amino]-2-fluoro-N-isopropyl-benzamide | 55 |
| 103 | 5-[(4-Chloro-benzyl)-(3-cyano-benzenesulfonyl)-amino]-2-fluoro-N-(2-hydroxy-ethyl)-benzamide | 99 |
| 104 | 5-[(4-Chloro-benzyl)-(3-cyano-benzenesulfonyl)-amino]-2-fluoro-N-(1-hydroxymethyl-propyl)-benzamide | 98 |
| 105 | N-(4-Chloro-benzyl)-3-cyano-N-[4-fluoro-3-(3-hydroxy-azetidine-1-carbonyl)-phenyl]-benzenesulfonamide | 50 |
| 106 | 5-[(4-Chloro-benzyl)-(3-cyano-benzenesulfonyl)-amino]-2-fluoro-N-(2-hydroxy-1-hydroxymethyl-ethyl)-benzamide | 77 |
| 107 | 5-[(4-Chloro-benzyl)-(3-cyano-benzenesulfonyl)-amino]-2-fluoro-N-(2-hydroxy-1-methyl-ethyl)-benzamide | 99 |
| 108 | 5-[(4-Chloro-benzyl)-(3-cyano-benzenesulfonyl)-amino]-2-fluoro-N-(2-hydroxy-1,1-dimethyl-ethyl)-benzamide | 99 |
| 109 | 5-[(4-Chloro-benzyl)-(3-cyano-benzenesulfonyl)-amino]-2-fluoro-N-(2-methoxy-ethyl)-benzamide | 99 |
| 110 | N-(4-Chloro-benzyl)-3-cyano-N-[4-fluoro-3-(3-hydroxy-piperidine-1-carbonyl)-phenyl]-benzenesulfonamide | 85 |
| 111 | N-(4-Chloro-benzyl)-3-cyano-N-[4-fluoro-3-((R)-3-hydroxy-pyrrolidine-1-carbonyl)-phenyl]-benzenesulfonamide | 41 |
| 112 | 3-[(4-Chloro-benzyl)-(pyridine-3-sulfonyl)-amino]-N-(2-hydroxy-ethyl)-benzamide | 65 |
| 113 | 3-[(4-Chloro-benzyl)-(pyridine-3-sulfonyl)-amino]-N-(2-hydroxy-1-methyl-ethyl)-benzamide | 70 |
| 114 | 3-[(4-Chloro-benzyl)-(pyridine-3-sulfonyl)-amino]-N-(1-hydroxymethyl-propyl)-benzamide | 45 |
| 115 | Pyridine-3-sulfonic acid (4-chloro-benzyl)-[3-(3-hydroxy-azetidine-1-carbonyl)-phenyl]-amide | 10 |
| 116 | Pyridine-3-sulfonic acid (4-chloro-benzyl)-[3-(3-hydroxy-piperidine-1-carbonyl)-phenyl]-amide | 13 |
| 117 | 3-[(4-Chloro-benzyl)-(pyridine-3-sulfonyl)-amino]-N-(2-hydroxy-1,1-dimethyl-ethyl)-benzamide | 91 |
| 118 | 3-[(4-Chloro-benzyl)-(pyridine-3-sulfonyl)-amino]-N-(2-methoxy-ethyl)-benzamide | 88 |
| 119 | 3-[(4-Chloro-benzyl)-(pyridine-3-sulfonyl)-amino]-N-cyclopropyl-benzamide | 98 |
| 120 | 3-[(4-Chloro-benzyl)-(pyridine-3-sulfonyl)-amino]-N-cyclopentyl-benzamide | 84 |
| 121 | Pyridine-3-sulfonic acid (4-chloro-benzyl)-[3-((R)-3-fluoro-pyrrolidine-1-carbonyl)-phenyl]-amide | 20 |
| 122 | 3-[(4-Chloro-benzyl)-(pyridine-3-sulfonyl)-amino]-N-cyclobutyl-benzamide | 97 |
| 123 | Pyridine-3-sulfonic acid [3-(azetidine-1-carbonyl)-phenyl]-(4-chloro-benzyl)-amide | 52 |
| 124 | 3-[(4-Chloro-benzyl)-(1-methyl-1H-imidazole-4-sulfonyl)-amino]-N-methyl-benzamide | 10 |
| 125 | 3-[(4-Chloro-benzyl)-(1-methyl-1H-imidazole-4-sulfonyl)-amino]-N-ethyl-benzamide | 54 |
| 126 | 3-[(4-Chloro-benzyl)-(1-methyl-1H-imidazole-4-sulfonyl)-amino]-N-(2-methoxy-ethyl)-benzamide | 21 |
| 127 | 3-[(4-Chloro-benzyl)-(1-methyl-1H-imidazole-4-sulfonyl)-amino]-N-cyclopropyl-benzamide | 49 |
| 128 | 3-[(4-Chloro-benzyl)-(1-methyl-1H-imidazole-4-sulfonyl)-amino]-N-cyclopentyl-benzamide | 69 |
| 129 | 3-[(4-Chloro-benzyl)-(1-methyl-1H-imidazole-4-sulfonyl)-amino]-N-cyclobutyl-benzamide | 57 |
| 130 | 1-Methyl-1H-imidazole-4-sulfonic acid [3-(azetidine-1-carbonyl)-phenyl]-(4-chloro-benzyl)-amide | 25 |
| 131 | 3-[(4-Chloro-benzyl)-(1-methyl-1H-pyrazole-3-sulfonyl)-amino]-N-methyl-benzamide | 78 |
| 132 | 3-[(4-Chloro-benzyl)-(1-methyl-1H-pyrazole-3-sulfonyl)-amino]-N-ethyl-benzamide | 99 |
| 133 | 3-[(4-Chloro-benzyl)-(1-methyl-1H-pyrazole-3-sulfonyl)-amino]-N-(2-methoxy-ethyl)-benzamide | 84 |
| 134 | 3-[(4-Chloro-benzyl)-(1-methyl-1H-pyrazole-3-sulfonyl)-amino]-N-cyclopropyl-benzamide | 97 |
| 135 | 3-[(4-Chloro-benzyl)-(1-methyl-1H-pyrazole-3-sulfonyl)-amino]-N-cyclobutyl-benzamide | 99 |
| 136 | 1-Methyl-1H-pyrazole-3-sulfonic acid [3-(azetidine-1-carbonyl)-phenyl]-(4-chloro-benzyl)-amide | 64 |
| 137 | 1-Methyl-1H-pyrazole-3-sulfonic acid (4-chloro-benzyl)-[3-(3-methyl-piperidine-1-carbonyl)-phenyl]-amide | 69 |
| 138 | 3-[(4-Chloro-benzyl)-(1-methyl-1H-pyrazole-3-sulfonyl)-amino]-N-cyclopentyl-benzamide | 100 |
| 139 | 3-[(4-Chloro-benzyl)-(1-methyl-1H-pyrazole-3-sulfonyl)-amino]-N-(2-hydroxy-1-methyl-ethyl)-benzamide | 50 |
| 140 | 3-[(4-Chloro-benzyl)-(1-methyl-1H-pyrazole-3-sulfonyl)-amino]-N-(1-hydroxymethyl-propyl)-benzamide | 70 |

-continued

| Example | Name | hKv1.5 % Inh. |
|---|---|---|
| 141 | 3-[(4-Chloro-benzyl)-(1-methyl-1H-pyrazole-3-sulfonyl)-amino]-N-(2-hydroxy-1,1-dimethyl-ethyl)-benzamide | 78 |
| 139 | 3-[(4-chloro-benzyl)-(2-methyl-2H-pyrazole-3-sulfonyl)-amino]-N-cyclobutyl-benzamide | 59 |
| 140 | 3-[(4-chloro-benzyl)-(2-methyl-2H-pyrazole-3-sulfonyl)-amino]-N-cyclopentyl-benzamide | 55 |

REFERENCES

Herbert, "General principles of the structure of ion channels" Am. J. Med. 104, 87-9, 1998.

Armstrong & Hille, "Voltage-gated ion channels and electrical excitability". Neuron, 20, 371-380, 1998.

Gutman G A et al., "International Union of Pharmacology. XLI. Compendium of voltage-gated ion channels: potassium channels". Pharmacol Rev. December; 55(4):583-6, 2003.

Shieh et al., "Potassium Channels: Molecular Defects, Diseases, and Therapeutic Opportunities", Pharmacol Rev, 52(4), 557-594, 2000.

Ford et al., "Potassium Channels: Gene Family, Therapeutic Relevance, High-Throughput Screening Technologies and Drug Discovery", Prog Drug Res, 58, 133-168, 2002.

Xie M et al., "Ion Channel Drug Discovery Expands into New Disease Areas", Current Drug Discovery, 31-33, 2004.

Cahalan M D & Chandy K G, "Ion Channels in the Immune System as Targets for Immunosuppression", Current Opinion in Biotechnology, 8, 749-756, 1997.

Becton et al., "Kv1.3 channels are a therapeutic target for T cell-mediated autoimmune diseases", Proceeds of the National Academy of Sciences, 46, 103, 17414-17419, 2006

Wulff H, Becton C, Chandy K G: Potassium channels as therapeutic targets for autoimmune disorders. (2003) Curr. Opin. Drug Dis. 6(5):640-647

Becton C, Pennington M W, Wulff H. Singh S, Nugent B, Crossley G, Khaytin I, Calabresi P A, Chen C Y, Gutman G A, Chandy K G. Targeting effector memory T cells with a selective peptide inhibitor of Kv1.3 channels for therapy of autoimmune diseases. (2005) Mol Pharmacol. 67(4): 1369-81.

Panyi G, Varga Z, Gaspar R. Abstract Ion channels and lymphocyte activation. (2004) Immunology Lett. 92:55-66.

Chandy K G, Wulff H, Becton C, Pennington M. Gutman G, Cahalan M: K+ channels as targets for specific immuno-modulation. TIPS. (2004) 25(5):280-289

Becton C, Barbaria J, Giraud P, Devaux J, Benolicl A, Gola M, Sabatier J M, Bernard D, Crest M, Beraud E: Selective blocking of voltage-gated K+ channel improves experimental autoimmune encephalomyclitis and inhibits T cell activation. (2001) J. Immunol. 166:936-944

Price M J, Lee S C, Deutsch C: Charybdotoxin inhibits proliferation and interleukin-2 production of human peripheral blood lymphocytes. (1989) Proc. Natl. Acad. Sci. 86:10171-10175

Koo G C, Blake J T, Shah K, Staruch M J, Dumont F. Wunderler D L, Sanchez M, McManus O B, Sirontina-Meisher A, Fischer P. Boltz R C, Goetz M A, Baker R, Bao J, Kayser F, Rupprecht K M, Parsons W H, Tong X, Ita I E, Pivnicluny J, Vincent S, Cunningham P. Hora D, Feeney W, Kaczorowski G, Springer M S: Correolide and derivatives are novel immunosuppressants blocking the lymphocyte Kv1.3 potassium channels. (1999). Cell. Immunol., 197:99-107

Schmitz A, Sankaranarayanan A, Azam P, Schmidt-Lassen K, Homeriek D, Hansel W, Wulff H: Design of PAP-1, a selective small molecule Kv1.3 blocker, for the suppression of effector memory cells in autoimmune diseases. (2005) Mol. Pharmacol, 68:1254-1270

Triggle D. J, Gopalakkrishnan M, Rampe D, Zheng W: Voltage gated Ion channels as Drug Targets, Wiley, 2005)

Sands et al,: Charabydotoxin blocks voltage-gated K+ channels in human and murine T lymphocytes. J. Gen-Physiol. 1989, 93, 10061-1074.

Garcia et al, Purification, characterisation and biosynthesis of margatoxin, component of *Centruroides maragritatas* venom that selectively inhibits voltage-gated potassium channels, J. Biol. Chem. 1993, 268, 18866-1887

Garcia et al.: Purification and characterisation of three inhibitors of voltage dependent K+ channels from *Leiurus quinquesttriatus* var. *hebracus*. Biochemistry, 1994, 33, 6834-6839

Koshehak et al., Subunit composition of brain voltage-gated potassium channels determined by hongotoxin-1, a novel peptide derived from *Centruroides limbatus* venom. J. Biol. Chem. 1998, 273, 2639-2644.

Peter et al, Effect of toxins Pi2 and Pi3 on human T Lymphocyte kv1.3 channels: the role of Glu7 and Lys24: J. Membr. Biol. 2001, 179, 13-25

Mouhat et al, K+ channel types targeted by synthetic DSK1, a toxin from *Orthochirus scrobiculosus* scorpion venom Biochem. J. 2005, 385, 95-104

Pennington et al, Identification of there separate binding sites on Shk toxin, a potent inhibitor of voltage dependent potassium channels in human T-lymphocytes and rat brain. Biochem. Biophys. Res. Commun. 1996, 219, 696-701

Pennington et al, ShK-Dap[22], to potent Kv1.3-specific immunosuppressive polypeptide. J. Biol. Chem. 1998, 273, 32697-35707

Nguyen A et al., "Novel Nonpeptide Agents Potently Block the C-Type InActivated Conformation of Kv1.3 and Suppress T Cell Activation", Mol, Pharmacol., 50, 1672-1679, 1996.

Hanson D C et al., "UK-78,282, a Novel Piperidine Compound That Potently Blocks the Kv1.3 Voltage-Gated Potassium Channel and Inhibits Human T Cell Activation", Br. J. Pharmacol., 126, 1707-1716, 1999.

Felix J P et al., "Identification and Biochemical Characterization of a Novel Norterpene Inhibitor of the Human Lymphocyte Voltage-Gated Potassium Channel, Kv1.3", Biochemistry, 38(16), 4922-4930, 1999.

Buell J B et al., "Khellinone Derivatives as Blockers of the Voltage-Gated Potassium Channel Kv1.3: Synthesis and Immunosuppressive Activity" J. Med. Chem., 47, 2326-2336, 2004.

Wulff H et al., "Alkoxypsoralens, Novel Nonpeptide Blockers of Shaker-Type K+ Channels: Synthesis and Photoreactivity", J. Med. Chem., 41, 4542-4549, 1998.

Vennekamp J, Wulff H, Becton C, Calabresi P A, Grissmer S, Hansel W, and Chandy K G, Kv1.3-blocking 5-phenylalkoxypsoralens: a new class of immunomodulators. (2004) Mol. Pharmacol. 65, 1364-74.

Marban "Cardiac channelepalthies", Nature, 415, 213-218, 213-218, 2002
Brendel and Peukert 'Blockers of the Kv1.5 Channel for the Treatment of Atrial Arrhythmias', Expert Opinion in Therapeutic Patents, 12 (11), 1159-1598 (2002).
Wang et al., "Sustained depolarizatirin-induced outward current in human atrial myocytes. Evidence for a novel delayed rectifier K+ current similar to Kv1.5 cloned channel currents", Circ Res, 73, 1061-107, 1993.
Fedida at al., "Identity of a novel delayed rectifier current from human heart with a cloned K+ channel current", Circ Res, 73, 210-216, 1993.
Feng et al., "Antisense oligodeoxynucleotides directed against Kv1.5 mRNA specifically inhibit ultrarapid delayed rectifier K+ current in cultured adult human atrial myocytes", Circ Res, 80, 572-579, 1997.
Amos at al., "Differences between outward currents of human atrial and subepicardial ventricular myocytes", Physiol 491, 31-50, 1996.
Li et al, "Evidence for two components of delayed rectifier K+ current in human ventricular myocytes", Circ Res, 78, 689-696, 1996.
Nattel, 'Therapeutic implications of atrial fibrillation mechanisms: can mechanistic insights be used to improve AF management?' Cardiovascular Research, Volume 54, (2), 347-360, 2002.
Courtemanche et al., "Ionic targets for drug therapy and atrial fibriilation-induced electrical remodeling: insights from a mathematical model", Cardiovasc Res, 42(2), 477-489, 1999.
Nattel et al., "Cardiac ultrarapid delayed rectifiers: a novel potassium current family of functional similarity and molecular diversity", Cell Physiol Biochem, 9(4-5), 217-216, 1999.
Knobloch K. et al. Electrophysiological and antiarrhythmic effects of the novel I(Kur) channel blockers, S9947 and S20951, on left vs. right pig atrium in vivo in comparison with the I(Kr) blocker, dofetilide, azimilide, d,l-sotalol and ibutilide. Naunyn Schmiedebergs Arch Pharmacol. November; 366(5):482-7, 2002.
Wirth K J et al., Atrial effects of the novel K(+)-channel-blocker AVE0118 in anesthetized pigs. Cardiovasc Res. November 1; 60 (2):298-306, 2003.
Colatsky et al., "Channel specificity in antiarrhythmic drug action. Mechanism of potassium channel block and its role in suppressing and aggravating cardiac arrhythmias", Circulation, 82(6), 2235-2242, 1990.
Feng et al., "Effects of class III antiarrhythmic drugs on transient outward and ultra-rapid delayed rectifier currents in human atrial myocytes", J. Pharmacol Exp Ther, 281(1), 384-392, 1997.
Wang et al., "Effects of flecainide quinidine, and 4-aminopyridine on transient outward and ultrarapid delayed rectifier currents in human atrial myocytes", J Pharmacol, 272(1), 184-196, 1995.
Malayev et al., "Mechanism of clofilium block of the human Kv1.5 delayed rectifier potassium channel", Mol Pharmaco, 147(1), 198-205, 1995.
Godreau et al., "Mechanisms of action of antiarrhythmic agent bertosamil on hKv1.5 channels and outward potassium current in human atrial myocytes", J Pharmacol Exp Ther 300(2), 612-620, 2002.
Matsuda et al., "Inhibition by a novel anti-arrythmic agent, NIP-142, of cloned human cardiac K+channel Kv1.5 current", Life Sci, 68, 2017-2024, 2001.
Bachmann et al., "Characterization of a novel Kv1.5 channel blocker in *Xenopus oocytes*, CHO cells, human and rat cardiomyocytes", Naunyn Schmiedebergs Arch Pharmacol, 364(5), 472-478, 2001.
Peukert S. et al., Identification, synthesis, and activity of novel blockers of the voltage-gated potassium channel Kv1.5. J Med Chem. February 13; 46(4):486-98, 2003.

The invention claimed is:
1. A compound of formula (I):

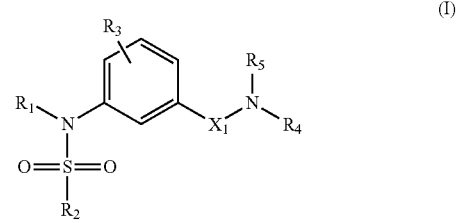

or its salts or pharmaceutically acceptable derivatives thereof;
wherein:
$X_1$ is selected from a group consisting of $CH_2$, C(=O), C(=NH), and NHC(=O);
$R_1$ is selected from the group consisting of optionally substituted arylalkyl, and optionally substituted heteroarylalkyl;
$R_2$ is selected from the group consisting of optionally substituted aryl, heteroaryl, and $NR_{24}R_{25}$;
$R_3$ is selected from the group consisting of hydrogen, halogen, hydroxy, alkoxy, aryloxy, optionally substituted alkyl, optionally substituted amino, optionally substituted amino sulfonyl, and nitrile;
$R_4$ is selected from the group consisting of optionally substituted cycloalkyl, optionally substituted heterocycloalkyl, optionally substituted aryl, optionally substituted arylalkyl, and optionally substituted heteroaryl;
$R_5$ is selected from the group consisting of hydrogen and optionally substituted alkyl;
$R_{24}$ and $R_{25}$ are the same or different and each represents hydrogen, optionally substituted alkyl, optionally substituted cycloalkyl, optionally substituted arylalkyl, optionally substituted aryl or optionally substituted heteroaryl;
m=1, 2 or 3;
with the proviso that when $X_1$ is C=O and $R_5$ is H then $R_4$ is not:

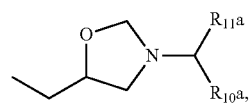

wherein
$R_{10}a$ is H or $C_{1-6}$alkyl; and
$R_{11}a$ is $C_{1-6}$alkyl or aryl-$C_{1-6}$alkyl; and
wherein optionally substituted means a group may be substituted by one or more substituents, which may be the same or different, and which are selected from alkyl, cycloalkyl, —OC(halogen)$_3$, biaryl, carbocyclic aryl, heteroalicyclic, heteroaryl, acyl, amidino, amido, amino, alkyloxyamino, carbamoyl, carboxy, cyano, ether, hydroxyl, imino, halo, nitro, sulphamoyl, sulfonyl, sulphinyl, sulphenyl, sulfonamido, and urea.

2. A compound according to claim 1, wherein $X_1$ is $C(=O)$.

3. A compound according to claim 2, wherein $R_2$ is $NR_{24}R_{25}$.

4. A compound according to claim 3, wherein $R_{24}$ and $R_{25}$ are the same or different and each represents hydrogen, or optionally substituted $C_{1-3}$ alkyl.

5. A compound according to claim 2, wherein $R_2$ is selected from formula (III), (IV) and (V):

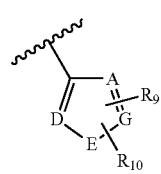
(III)

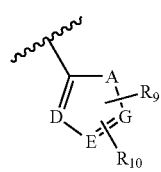
(IV)

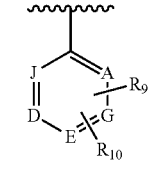
(V)

wherein:
A, D, E, G, and J are the same or different and each represents C or N with the provisos that in each instance
1) at least one of A, D, E, G, or J is N;
2) when $R_2$ is formula (III), E may also represent O or S; and
3) when $R_2$ is formula (IV), A may also represent O or S;
$R_9$ and $R_{10}$ are the same or different and each represents hydrogen, halogen, hydroxy, nitrile, optionally substituted amino, optionally substituted acyl, optionally substituted $C_{1-3}$ alkyl, optionally substituted arylalkyl, optionally substituted aryl or optionally substituted heteroaryl or may be taken together to form an optionally substituted saturated or partially saturated 5-7 membered heterocyclic or carbocyclic ring.

6. A compound according to claim 2, wherein $R_2$ is formula (VI):

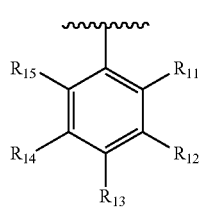
(VI)

wherein $R_{11}$, $R_{12}$, $R_{13}$, $R_{14}$, and $R_{15}$ are the same or different and each represents hydrogen, halogen, hydroxy, optionally substituted amino, optionally substituted acyl, nitrile, and optionally substituted $C_{1-3}$ alkyl or any of the pairs $R_{11}$ and $R_{12}$, or $R_{12}$ and $R_{13}$, or $R_{13}$ and $R_{14}$, or $R_{14}$ and $R_{15}$ may be taken together to form an optionally substituted saturated or partially saturated 5-7 membered heterocyclic or carbocyclic ring.

7. A compound according to claim 1, wherein $R_1$ has the formula (VII):

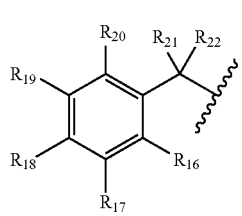
(VII)

wherein:
$R_{16}$, $R_{17}$, $R_{18}$, $R_{19}$ and $R_{20}$ are the same or different and each represents hydrogen, halogen, hydroxy, optionally substituted amino, optionally substituted acyl, nitrile, optionally substituted $C_{1-3}$ alkyl or optionally substituted alkoxy; and
$R_{21}$ and $R_{22}$ are the same or different and each represents hydrogen, hydroxy, and optionally substituted $C_{1-3}$ alkyl.

8. A compound according to claim 1, wherein $R_3$ is H, F, or $CH_3$.

9. A compound according to claim 8, wherein $R_3$ is H or F.

10. A compound according to claim 1, wherein $R_4$ is selected from the group consisting of cyclopropyl, cyclopropylmethyl, cyclobutyl, cyclopentyl, -phenyl, benzyl, phenethyl, 3-phenylpropyl, indazolyl, pyridyl, thiadiazolyl, and thiazolyl, each of which is optionally substituted.

11. A compound according to claim 1, wherein $R_5$ is hydrogen or $CH_3$.

12. A compound according to claim 1, wherein the compound is of formula (VIII):

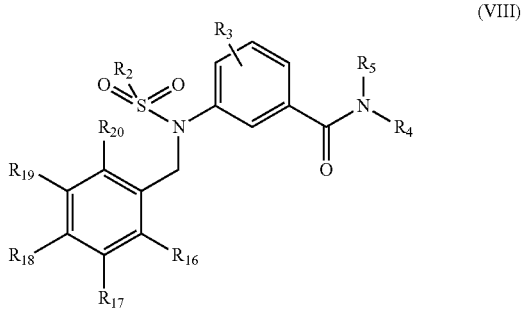
(VIII)

wherein:
$R_2$ is selected from the group consisting of $NR_{24}R_{25}$, formula (III), formula (IV), formula (V), and formula (VI):

(III)

(IV)

(V)

(VI)

wherein:

A, D, E, G, and J are the same or different and each is C or N, with the provisos that in each instance:
1) at least one of A, D, E, G, or J is N;
2) when $R_2$ is formula (III), E may also be O or S; and
3) when $R_2$ is formula (IV), A may also be O or S;

$R_9$ and $R_{10}$ are the same or different and each is hydrogen, halogen, hydroxy, cyano, amino, acyl, optionally substituted $C_{1-3}$ alkyl, optionally substituted arylalkyl, optionally substituted aryl, or optionally substituted heteroaryl; or may be taken together to form an optionally substituted saturated or partially saturated 5-7 membered heterocyclic or carbocyclic ring;

$R_{11}$, $R_{12}$, $R_{13}$, $R_{14}$, and $R_{15}$ are the same or different and each represents hydrogen, halogen, hydroxy, amino, acyl, cyano, and optionally substituted $C_{1-3}$alkyl, or any of the pairs $R_{11}$ and $R_{12}$, or $R_{12}$ and $R_{13}$, or $R_{13}$ and $R_{14}$, or $R_{14}$ and $R_{15}$ may be taken together to form an optionally substituted saturated or partially saturated 5-7 membered heterocyclic or carbocyclic ring; and $R_{16}$, $R_{17}$, $R_{18}$, $R_{19}$ and $R_{20}$ are the same or different and each represents hydrogen, halogen, hydroxy, amino, acyl, cyano, optionally substituted $C_{1-3}$ alkyl, or optionally substituted alkoxy.

13. A compound according to claim 12, wherein the compound is of formula (IX):

(IX)

14. A compound according to claim 1 selected from the group consisting of:
3-(Benzenesulfonyl-benzyl-amino)-N-(1H-indazol-6-yl)-benzamide;
3-(Benzenesulfonyl-benzyl-amino)-N-pyridin-2-ylmethyl-benzamide;
3-(Benzenesulfonyl-benzyl-amino)-N-(1H-indazol-5-yl)-benzamide;
3-(Benzenesulfonyl-benzyl-amino)-N-(4-imidazol-1-yl-phenyl)-benzamide;
3-(Benzenesulfonyl-benzyl-amino)-N-(4-pyrazol-1-yl-phenyl)-benzamide;
3-(Benzenesulfonyl-benzyl-amino)-N-[1,3,4]thiadiazol-2-yl-benzamide;
3-(Benzenesulfonyl-benzyl-amino)-N-thiazol-2-yl-benzamide;
N-[4-(Aminocarbonyl)phenyl]-3-[benzyl(phenylsulfonyl)amino]benzamide;
N-[3-(Aminocarbonyl)phenyl]-3-[benzyl(phenylsulfonyl)amino]benzamide;
3-(Benzenesulfonyl-benzyl-amino)-N-phenyl-benzamide;
N-Benzyl-2-fluoro-N-[3-(morpholine-4-carbonyl)-phenyl]-benzenesulfonamide;
N-Benzyl-4-fluoro-N-[3-(morpholine-4-carbonyl)-phenyl]-benzenesulfonamide;
3-(Benzenesulfonyl-benzyl-amino)-N-cyclopropyl-benzamide;
3-(Benzenesulfonyl-benzyl-amino)-N-cyclobutyl-benzamide;
3-(Benzenesulfonyl-benzyl-amino)-N-cyclopentyl-benzamide;
3-[(4-Chloro-benzyl)-(pyridine-3-sulfonyl)-amino]-N-cyclopropyl-benzamide;
3-[(4-Chloro-benzyl)-(pyridine-3-sulfonyl)-amino]-N-cyclopentyl-benzamide;
3-[(4-Chloro-benzyl)-(pyridine-3-sulfonyl)-amino]-N-cyclobutyl-benzamide;
3-[(4-Chloro-benzyl)-(1-methyl-1H-imidazole-4-sulfonyl)-amino]-N-cyclopropyl-benzamide;
3-[(4-Chloro-benzyl)-(1-methyl-1H-imidazole-4-sulfonyl)-amino]-N-cyclopentyl-benzamide;
3-[(4-Chloro-benzyl)-(1-methyl-1H-imidazole-4-sulfonyl)-amino]-N-cyclobutyl-benzamide;
3-[(4-Chloro-benzyl)-(1-methyl-1H-pyrazole-3-sulfonyl)-amino]-N-cyclopropyl-benzamide;
3-[(4-Chloro-benzyl)-(1-methyl-1H-pyrazole-3-sulfonyl)-amino]-N-cyclobutyl-benzamide;
3-[(4-Chloro-benzyl)-(1-methyl-1H-pyrazole-3-sulfonyl)-amino]-N-cyclopentyl-benzamide;
3-[(4-Chloro-benzyl)-(2-methyl-2H-pyrazole-3-sulfonyl)-amino]-N-cyclobutyl-benzamide; and 3-[(4-Chloro-benzyl)-(2-methyl-2H-pyrazole-3-sulfonyl)-amino]-N-cyclopentyl-benzamide, or a pharmaceutically acceptable salt thereof.

15. A pharmaceutical composition comprising at least one compound of claim 1 optionally together with one or more pharmaceutically acceptable excipients, diluents and/or carriers.

16. A method for the treatment of a disorder which requires potassium channel inhibition, comprising administering to a subject an effective amount of the compound of claim 1, wherein the disorder is psoriasis, rheumatoid arthritis, multiple sclerosis, or arrhythmia.

17. A method according to claim 16, wherein the disorder is psoriasis.

18. A method according to claim 16, wherein the disorder is rheumatoid arthritis.

19. A method according to claim 16, wherein the disorder is multiple sclerosis.

20. A method according to claim 16, wherein the disorder is arrhythmia.

* * * * *